(12) United States Patent
Dixit et al.

(10) Patent No.: US 7,115,260 B2
(45) Date of Patent: *Oct. 3, 2006

(54) INTERLEUKIN-1β CONVERTING ENZYME LIKE APOPTOTIC PROTEASE-6

(75) Inventors: Vishva M. Dixit, Los Altos Hills, CA (US); Wei-Wu He, Columbia, MD (US); Kristine K. Kikly, Linfield, PA (US); Steven M. Ruben, Brookeville, MD (US)

(73) Assignees: Human Genome Sciences, Inc., Rockville, MD (US); SmithKline Beecham Corporation, Philadelphia, PA (US); The Regents of the University of Michigan, Ann Arbor, MI (US)

( * ) Notice: Subject to any disclaimer, the term of this patent is extended or adjusted under 35 U.S.C. 154(b) by 23 days.

This patent is subject to a terminal disclaimer.

(21) Appl. No.: 10/961,148

(22) Filed: Oct. 12, 2004

(65) Prior Publication Data

US 2005/0089984 A1    Apr. 28, 2005

Related U.S. Application Data

(62) Division of application No. 09/961,201, filed on Sep. 24, 2001, now Pat. No. 6,890,721, which is a division of application No. 09/300,328, filed on Apr. 27, 1999, now Pat. No. 6,294,169, which is a division of application No. 08/852,936, filed on May 8, 1997, now Pat. No. 6,010,878.

(60) Provisional application No. 60/018,961, filed on Jun. 5, 1996, provisional application No. 60/020,344, filed on May 23, 1996, provisional application No. 60/017,949, filed on May 20, 1996.

(51) Int. Cl.
  *A61K 38/17*   (2006.01)
  *A61K 38/18*   (2006.01)
  *A61K 39/00*   (2006.01)
  *C12P 21/00*   (2006.01)

(52) U.S. Cl. ............... 424/94.1; 424/185.1; 424/192.1; 435/69.1; 530/350

(58) Field of Classification Search ................. 530/350; 424/94.64, 192.1
See application file for complete search history.

(56) References Cited

U.S. PATENT DOCUMENTS 6,010,878 A * 1/2000 Dixit et al. ................. 435/69.1
6,294,169 B1 * 9/2001 Dixit et al. ............... 424/94.65

FOREIGN PATENT DOCUMENTS

WO    WO-93/00353    1/1993

OTHER PUBLICATIONS

Ngo et al., in The Protein Folding Problem and Tertiary Structure Prediction, 1994, Merz, et al., (ed.), Birkhauser, Boston, MA, pp. 491-495.*

Attwood et al., The babel of bioinformatics, Oct. 2000, Science 290 (5491): 471-473.*

Stryer et al, in Biochemistry, Third edition, W H Freeman Company, New York, pp. 31-33, 1998.*

Duan et al., "ICE-LAP3, a Novel Mammalian Homologue of the Caenorhabditis elegans Cell Death Protein Ced-3 Is Activated during Fas- and Tumor Necrosis Factor-induced Apoptosis," The Journal of Biological Chemistry, vol. 271 (3), pp. 1621-1625 (1996).

Fernandes-Alnemri et al., "Mch3, a Novel Human Apoptotic Cysteine Protease Highly Related to CPP32," Cancer Research, vol. 55, pp. 6045-6052 (1995).

GenBank Accession No. H39637, Aug. 4, 1995, Hillier, L. et al., Homo Sapiens cDNA Clone 1819835.

GenBank Accession No. T97582, Apr. 16, 1995, Hillier, L. et al., Homo Sapiens cDNA Clone 1216935.

Duan et al., "ICE-LAP6, a Novel Member of the ICE/CED-3 Gene Family, Is Activated by the Cytotoxic T Cell Protease Granzyme B," The Journal of Biological Chemistry, vol. 271 (28), pp. 16720-16724 (1996).

(Continued)

*Primary Examiner*—Christina Chan
*Assistant Examiner*—Phuong Huynh
(74) *Attorney, Agent, or Firm*—Human Genome Sciences, Inc.

(57) ABSTRACT

Human ICE LAP-6 polypeptides and DNA (RNA) encoding such ICE LAP-6 and a procedure for producing such polypeptides by recombinant techniques is disclosed. Also disclosed are methods for utilizing such ICE LAP-6 for the treatment of a susceptibility to viral infection, tumorogenesis and to diseases and defects in the control embryogenesis and tissue homeostasis, and the nucleic acid sequences described above may be employed in an assay for ascertaining such susceptibility. Antagonists against such ICE LAP-6 and their use as a therapeutic to treat Alzheimer's disease, Parkinson's disease, rheumatoid arthritis, septic shock, sepsis, stroke, chronic inflammation, acute inflammation, CNS inflammation, osteoporosis, ischemia reperfusion injury, cell death associated with cardiovascular disease, polycystic kidney disease, apoptosis of endothelial cells in cardiovascular disease, degenerative liver disease, MS, ALS, cerebellar degeneration, ischemic injury, myocardial infarction, AIDS, myelodysplastic syndromes, aplastic anemia, male pattern baldness, and head injury damage are also disclosed. Also disclosed are diagnostic assays for detecting diseases related to mutations in the nucleic acid sequences and altered concentrations of the polypeptides. Also disclosed are diagnostic assays for detecting mutations in the polynucleotides encoding the interleukin-1 beta converting enzyme apoptosis proteases and for detecting altered levels of the polypeptide in a host.

26 Claims, 7 Drawing Sheets

OTHER PUBLICATIONS

Srinivasula et al., "The Ced-3/Interleukin 1-beta Converting Enzyme-like Homolog Mch6 and the Lamin-cleaving Enzyme Mch2-alpha Are Substrates for the Apoptotic Mediator CPP32," The Journal of Biological chemistry, vol. 271 (43), pp. 27099-27106 (1996).

Orkin et al., "Report and recommendations of the panel to assess the NIH investment in research on gene therapy," issued by the U.S. Nation Institutes of Health, Dec. 1995.

Ngo et al., "Computational complexity, protein structure prediction, and the Levinthal paradox," The Protein Folding Problem and Teriary Structure Prediction, Merx et al., Birkhauser Boston: Boston MA, pp. 433 and 492-495 (1994).

Fernandes-Alnemri et al., "CPP32, a novel human apoptotic protein with homology to Caenorhabditis elegans cell death protein ced-3 and mammalian interleukin-1 beta converting enzyme," Journal of Biological Chemistry, vol. 269 (49), pp. 30761-30764 (1994).

Cryns et al., "The cutting edge: caspases in apoptosis and disease," pp. 177-210, When Cells Die, eds. Lockshin et al. New York: Willey-Liss, Inc. (1998).

Pa Henkart, "ICE family proteases: mediators of all apoptotic cell death?," Immunity vol. 4, pp. 195-201, (1996).

Alnemri et al., "Cloning and Expression of four novel isoforms of human interleukin-1beta converting enzyme with different apoptotic activities," Journal of Biological Chemistry, Mar. 3, 1995, vol. 270, No. 9, pp. 4312-4317.

Tewari et al., "Yama/CPP32beta, a mammalian homolog of ced-3 is a crmA-inhibitable protease that cleaves the death substrate poly (ADP-ribose) polymerase," Cell, Jun. 2, 1995, vol. 81, No. 5, pp. 801-809.

Wang et al., "Ich-1, an ICE/ced-3 related gene, encodes both positive and negative regulators of programmed cell death," Cell Sep. 9, 1994, vol. 78, pp. 739-750.

Thornberry et al., "Interleukin-1beta-converting enzyme and related proteases as potential targets in inflammation and apoptosis," Perspectives in Drug Discovery and Design, Jul. 1995, vol. 2, No. 3, pp. 389-399.

Kamens et al, "Identification and characterization of ICH-2, a novel member of the interleukin-1beta-converting family of cysteine proteases," Journal of Biological Chemistry, Jun. 23, 1995, vol. 270, No. 25, pp. 15250-15256.

* cited by examiner

MDEADRRLLRRCRLRLVEELQVDQLWDVLLSRELFRPHMIEDIQRAGSGSRRDQA
RQLIIDLETRGSQAL
PLFISCLEDTGQDMLASFLRTNRQAGKLSKPTLENLTPVVLRPEIRKPEVLRPETPR
PVDIGSGGFGDVG
ALESLRGNADLAYILSMEPCGHCLIINNVNFCRESGLRTRTGSNIDCEKLRRRFSSL
HFMVEVKGDLTAK
KMVLALLELARQDHGALDCCVVVILSHGCQASHLQFPGAVYGTDGCPVSVEKIVNI
FNGTSCPSLGGKPK
LFFIQACGGEQKDHGFEVASTSPEDESPGSNPEPDATPFQEGLRTFDQLDAISSLP
TPSDIFVSYSTFPG
FVSWRDPKSGSWYVETLDDIFEQWAHSEDLQSLLLRVANAVSVKGIYKQMPGCFN
FLRKKLFFKTS

FIG. I

```
  1 GCCATGGACG AAGCGGATCG GCGGCTCCTG CGGCGGTGCC GGCTGCGGCT

51 GGTGGAAGAG CTGCAGGTGG ACCAGCTCTG GACGTCCTG CTGAGCCGCG

101 AGCTGTTCAG GCCCCATATG ATCGAGGACA TCCAGCGGGC AGGCTCTGGA

151 TCTCGGCGGG ATCAGGCCAG GCAGCTGATC ATAGATCTGG AGACTCGAGG

201 GAGTCAGGCT CTTCCTTTGT TCATCTCCTG CTTAGAGGAC ACAGGCCAGG

251 ACATGCTGGC TTCGTTTCTG CGAACTAACA GGCAAGCAGG AAAGTTGTCG

301 AAGCCAACCC TAGAAAACCT TACCCCAGTG GTGCTCAGAC CAGAGATTCG

351 CAAACCAGAG GTTCTCAGAC CGGAAACACC CAGACCAGTG GACATTGGTT

401 CTGGAGGATT CGGTGATGTC GGTGCTCTTG AGAGTTTGAG GGGAAATGCA

451 GATTTGGCTT ACATCCTGAG CATGGAGCCC TGTGGCCACT GCCTCATTAT

501 CAACAATGTG AACTTCTGCC GTGAGTCCGG GCTCCGCACC CGCACTGGCT

551 CCAACATCGA CTGTGAGAAG TTGCGGCGTC GCTTCTCCTC GCTGCATTTC

601 ATGGTGGAGG TGAAGGGCGA CCTGACTGCC AAGAAAATGG TGCTGGCTTT

651 GCTGGAGCTG GCGCGGCAGG ACCACGGTGC TCTGGACTGC TGCGTGGTGG

701 TCATTCTCTC TCACGGCTGT CAGGCCAGCC ACCTGCAGTT CCCAGGGGCT
```

FIG. 2A

751 GTCTACGGCA CAGATGGATG CCCTGTGTCG GTCGAGAAGA TTGTGAACAT

801 CTTCAATGGG ACCAGCTGCC CCAGCCTGGG AGGGAAGCCC AAGCTCTTTT

851 TCATCCAGGC CTGTGGTGGG GAGCAGAAAG ACCATGGGTT TGAGGTGGCC

901 TCCACTTCCC CTGAAGACGA GTCCCCTGGC AGTAACCCCG AGCCAGATGC

951 CACCCCGTTC CAGGAAGGTT TGAGGACCTT CGACCAGCTG GACGCCATAT

1001 CTAGTTTGCC CACACCCAGT GACATCTTTG TGTCCTACTC TACTTTCCCA

1051 GGTTTTGTTT CCTGGAGGGA CCCCAAGAGT GGCTCCTGGT ACGTTGAGAC

1101 CCTGGACGAC ATCTTTGAGC AGTGGGCTCA CTCTGAAGAC CTGCAGTCCC

1151 TCCTGCTTAG GGTCGCTAAT GCTGTTTCGG TGAAAGGGAT TTATAAACAG

1201 ATGCCTGGTT GCTTTAATTT CCTCCGGAAA AAACTTTTCT TTAAAACATC

1251 ATAAGGCCAG GGCCCCTCAC CCTGCCTTAT CTTGCACCCC AAAGCTTTCC

1301 TGCCCCAGGC CTGAAAGAGG CTGAGGCCTG GACTTTCCTG CAACTCAAGG

1351 ACTTTGNAGC CGGCACAGGG TCTGCTCTTT CTCTGCCAGT GACAGACAGG

1401 CTCTTAGCAG CTTCCAGATT GACGACAAGT GCTGAACAGT GGAGGAAGAG

1451 GGACAGATGA ATGCCGTGGA TTGCACGTGG NCTCTTGAGC AGTGGCTGGT

FIG. 2B

1501 CCAGGGCTAG TGACTTGGTG TCCCATGATC CTGTGTTGG TCTCTAGGAG

1551 CAGGGATTAA CCTCTGCACT ACTGACAT

FIG. 2C

```
CTGACTGCCAAGAAAATGGTGCTGGCTTTGCTGGAGCTGG 40
CGCGGCAGGACCACGGTGCTCTGGACTGCTGCGTGGTGGT 80
CATTCTCTCTCACGGCTGTCAGGCCAGCCACCTGCAGTTC 120
CCAGGGGCTGTCTACGGCACAGATGGATGCCCTGTGTCGG 160
TCGAAAAGATTGTGAACATCTTCAATGGGACCAGCTGCCC 200
CAGCCTGGGAGGGAAGCCCAAGCTCTTTTTCATCCAGGCC 240
TGTGGTGGGGAGCAGAAAGACCATGGGTTTGAGGTGGCCT 280
CCACTTCCCCTGAAGACGAGTCCCTGGCAGTAACCCCGA 320
GCCAGATGCCACCCCGTTCCAGGAAGGTTTGAGGACCTTC 360
GACCAGCTGGACGCCATATCTAGTTTGCCCACACCCAGTG 400
ACATCTTTGTGTCCTACTCTACTTTCCCAGGTTTTGTTTC 440
CTGGAGGGACCCCAAGAGTGGCTCCTGGTACGTTGAGACC 480
CTGGACGACATCTTTGAGCAGTGGGCTCACTCTGAAGACC 520
TGCAGTCCCTCCTGCTTAGGGTCGCTAATGCTGTTTCGGT 560
GAAAGGGATTTATAAACAGATGCCTGGTTGCTTTAATTTC 600
CTCCGGAAAAAACTTTTCTTTTAAAACATCATAAGGCAG 639
```

FIG. 3

MVLALLELARQDHGALDCCV 20

VVILSHGCQASHLQFPGAVY 40

GTDGCPVSVEKIVNIFNGTS 60

CPSLGGKPKLFFIQACGGEQ 80

KDHGFEVASTSPEDESPGSN 100

PEPDATPFQEGLRTFDQLDA 120

ISSLPTPSDIFVSYSTFPGF 140

VSWRDPKSGSWYVETLDDIF 160

EQWAHSEDLQSLLLRVANAV 180

SVKGIYKQMPGCFNFLRKKL 200

FFM 203

INTERLEUKIN-1β CONVERTING ENZYME LIKE APOPTOTIC PROTEASE-6

RELATED APPLICATIONS

This application is a divisional of application Ser. No. 09/961,201, filed Sep. 24, 2001, now U.S. Pat. No. 6,890,721 which is a divisional of application Ser. No. 09/300,328, filed Apr. 27, 1999 (now U.S. Pat. No. 6,294,169), which is a divisional of U.S. application Ser. No. 08/852,936, filed May 8, 1997 (now U.S. Pat. No. 6,010,878), which claims the benefit of U.S. Provisional Application Nos. 60/018,961, filed Jun. 5, 1996, 60/020,344, filed May 23, 1996 and 60/017,949, filed May 20, 1996.

FIELD OF INVENTION

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human interleukin-1 beta converting enzyme apoptosis protease-6, hereinafter referred to as "ICE LAP-6".

BACKGROUND OF THE INVENTION

It has recently been discovered that an interleukin-1β converting enzyme (ICE) is responsible for cleaving pro-IL-1β into mature and active IL-1β and is also responsible for programmed cell death (or apoptosis), which is a process through which organisms get rid of unwanted cells.

Apoptosis, or programmed cell death, is a physiologic process important in the normal development and homeostasis of metazoans.

In the nematode *Caenorhabditis elegans*, a genetic pathway of programmed cell death has been identified (Ellis, R. E., et al. Annu. Rev. Cell Biol., 7:663–698 (1991)). Two genes, ced-3 and ced-4, are essential for cells to undergo programmed cell death in *C. elegans* (Ellis, H. M., and Horvitz, H. R., Cell, 44:817–829 (1986)). It is becoming apparent that a class of cysteine proteases homologous to *Caenorhabditis elegans* Ced-3-play the role of "executioner" in the apoptotic mechanism (Martin, S. J., and Green, D. R. (1995) Cell 82, 349–352; Chinnaiyan, A. a. D., VM. (1996) Current Biology 6; Henkart, P. (1996) Immunity 4, 195–201). Recessive mutations that eliminate the function of these two genes prevent normal programmed cell death during the development of *C. elegans*. The known vertebrate counterpart to ced-3 protein is ICE. The overall amino acid identity between ced-3 and ICE is 28%, with a region of 115 amino acids (residues 246–360 of ced-3 and 164–278 of ICE) that shows the highest identity (43%). This region contains a conserved pentapeptide, QACRG (residues 356–360 of ced-3), which contains a cysteine known to be essential for ICE function.

The similarity between ced-3 and ICE suggests not only that ced-3 might function as a cysteine protease but also that ICE alight act as a vertebrate programmed cell death gene. ced-3 and the vertebrate counterpart, ICE, control programmed cell death during embryonic development, (Gagliarnini, V. et al., Science, 263:826:828 (1994).

Mutations of ced-3 and ced-4 abolish the apoptotic capability of cells that normally die during *C. elegans* embryogenesis (Yuan, J. Y., and Horvitz, H. R. (1990) Dev Biol 138, 33–41). While no mammalian homologs of ced-4 have been identified, ced-3 shares sequence similarity with interleukin-1b. converting enzyme (ICE) (Yuan, J. et al (1993) Cell 75, 641–652), a cysteine protease involved in the processing and activation of pro-IL-1b to an active cytokine (Cerretti, D. P., et al (1992) Science 256, 97–100, Thornberry, N. A., et al (1992) Nature 356, 768–774). Recently, numerous homologs of ICE/Ced-3 have been characterized, comprising a new gene family of cysteine proteases. To date, seven members of the ICE/Ced-3 family have been identified and include ICE (Cererti, D. P., et al (1992) Science 256, 97–100), TX/ICH2/ICE rel-II (Munday, N. A., et al (1995) J Biol Chem 270, 15870–15876; Faucheu, C. et al. (1995) Embo J 14, 1914–1922; Kamens, J et al. (1995) J Biol Chem 270, 15250–1525612), ICE rel-III (Munday, N. A., et al (1995) J Biol Chem 270, 15870–15876), ICH1/Nedd-2 (Kumar, S., et al. (1994) Genes and Development 8, 1613–1626; Wang, L., et al. (1994) Cell 78, 739–750), Yama/CPP32/Apopain (Tewari. M., et al. (1995) Cell 81, 801–809; Fernandes-Alnemri, T., et al. (1994) J. Biol. Chem. 269, 30761–30764; Nicholson, D. Wet al. (1995) Nature 376, 37–43), Mch2 Fernandes-Alnemri, T., et al. (1994) J. Biol. Chem. 269, 30761–30764) and ICE-LAP3/Mch3/CMH-1 (Duan, H., et al. (1996) J. Biol. Chem. 271, 35013–35035; Fernandes-Alnemri, T., et al. (1995) Cancer Research 55, 6045–6052; Lippke, J. A., et al. (1996) The Journal of Biological Chemistry 271, 1825–1828). All family members share sequence homology with ICE/Ced-3 and contain an active site QACRG pentapeptide in which the cysteine residue is catalytic. Ectopic expression of these proteases in a variety of cells causes apoptosis. Phylogenetic analysis of the ICE/ced-3 gene family revealed three subfamilies (Chinnaiyan, A. a. D., VM. (1996) Current Biology 6; uan, H., et al. (1996) J. Biol. Chem. 271, 35013–35035). Yama, ICE-LAP3, and Mch2 are closely related to *C. elegans* Ced-3 and comprise the Ced-3 subfamily. ICE and the ICE-related genes, ICE rel II, and ICE rel III form the ICE subfamily, while ICH1 and its mouse homologue, NEDD-2 form the NEDD-2 subfamily. Based on similarities with the structural prototype interleukin-1b converting enzyme, ICE/Ced-3 family members are synthesized as zymogens that are capable of being processed to form active heterodimeric enzymes (Thornberry, N. A., et al (1992) Nature 356, 768–774). It will be important to determine which family members are in fact activated in response to apoptotic stimuli. Previous studies have demonstrated that pro-Yama and pro-ICE-LAP3 are processed into active subunits in response to various death stimuli including engagement of Fas/APO-1 or treatment with staurosporine (Duan, H., et al. (1996) J. Biol. Chem. 271, 35013–35035; Chinnaiyan, A. M., et al. 1996) Journal of Biological Chemistry 271, 4573–4576). Further, the serine protease granzyme B, one of the major effectors of cytotoxic T cell-mediated apoptosis, was shown to directly activate Yama (but not ICE), in vitro (Quan, L. T., et al. (1996) PNAS 93, In Press; Darmon, A. J., et al. (1995) Nature 377, 446–448).

ICE mRNA has been detected in a variety of tissues, including peripheral blood monocytes, peripheral blood lymphocytes, peripheral blood neutrophils, resting and activated peripheral blood T lymphocytes, placenta, the B lymphoblastoid line CB23, and monocytic leukemia cell line THP-1 cells (Cerretti, D. P., et al., Science, 256:97–100 (1992)), indicating that ICE may have an additional substrate in addition to pro-IL-1β. The substrate that ICE acts upon to cause cell death is presently unknown. One possibility is that it may be a vertebrate homolog of the *C. elegans* cell death gene ced-4. Alternatively, ICE might directly cause cell death by proteolytically cleaving proteins that are essential for cell viability.

The mammalian gene bcl-2, has been found to protect immune cells called lymphocytes from cell suicide. Also, crmA, a cow pox virus gene protein product inhibits ICE's protein splitting activity.

Clearly, there is a need for factors that are useful for inducing apoptosis for therapeutic purposes, for example, as an antiviral agent, an anti-tumor agent and to control embryonic development and tissue homeostasis, and the roles of such factors in dysfunction and disease. Further, there is clear a need for factors that are useful for reducing or halting apoptosis for therapeutic purposes, for example, to treat diseases caused or associated with apoptosis, such as, particularly Alzheimer's disease, Parkinson's disease, rheumatoid arthritis, septic shock, sepsis, stroke, chronic inflammation, acute inflammation, CNS inflammation, osteoporosis, ischemia reperfusion injury, cell death associated with cardiovascular disease, polycystic kidney disease, apoptosis of endothelial cells in cardiovascular disease, degenerative liver disease, MS, ALS, cererbellar degeneration, ischemic injury, myocardial infarction, AIDS, myelodysplastic syndromes, brain damage, aplastic anemia, male pattern baldness, and head injury damage. There is a need, therefore, for identification and characterization of such factors that are interleukin-1 beta converting enzyme apoptosis proteases, and which can play a role in preventing, ameliorating or correcting dysfunctions or diseases.

SUMMARY OF THE INVENTION

Toward these ends, and others, it is an object of the present invention to provide polypeptides, inter alia, that have been identified as novel ICE LAP-6 by homology between the amino acid sequence set out in FIG. 1 or the polypeptide encoded by the deposited clone and known amino acid sequences of other proteins such as those sequences set out in FIGS. 2A–2C.

It is a further object of the invention, moreover, to provide polynucleotides that encode ICE LAP-6, particularly polynucleotides that encode the polypeptide herein designated ICE LAP-6 and the polynucleotide of the deposited clone.

In a particular preferred embodiment of this aspect of the invention the polynucleotide comprises the region encoding human ICE LAP-6 set forth in FIGS. 2A–2C.

In accordance with this aspect of the present invention there is provided an isolated nucleic acid molecule encoding a mature polypeptide expressed by the human cDNA in FIGS. 2A–2C or derived using the primers set forth in Example 1, or a polynucleotide encoding the polypeptide in FIG. 1 or derived from the polypeptide encoded by the deposited clone.

In accordance with this aspect of the invention there are provided isolated nucleic acid molecules encoding human ICE LAP-6, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of human ICE LAP-6.

It also is an object of the invention to provide ICE LAP-6 polypeptides, particularly human ICE LAP-6 polypeptides, that may be employed for therapeutic purposes, for example, to treat viral infection, as an anti-tumor agent and to control embryonic development and tissue homeostasis.

In accordance with this aspect of the invention there are provided novel polypeptides of human origin referred to herein as ICE LAP-6 as well as biologically, diagnostically or therapeutically useful fragments, variants and derivatives thereof, variants and derivatives of the fragments, and analogs of the foregoing.

Among the particularly preferred embodiments of this aspect of the invention are variants of human ICE LAP-6 encoded by naturally occurring alleles of the human ICE LAP-6 gene.

It is another object of the invention to provide a process for producing the aforementioned polypeptides, polypeptide fragments, variants and derivatives, fragments of the variants and derivatives, and analogs of the foregoing.

In a preferred embodiment of this aspect of the invention there are provided methods for producing the aforementioned ICE LAP-6 polypeptides comprising culturing host cells having expressibly incorporated therein an exogenously-derived human ICE LAP-6-encoding polynucleotide under conditions for expression of human ICE LAP-6 in the host and then recovering the expressed polypeptide. ICE LAP-6 may also be purified from natural sources using any of many well known techniques.

In accordance with another object the invention there are provided products, compositions, processes and methods that utilize the aforementioned polypeptides and polynucleotides for research, biological, clinical, diagnostic and therapeutic purposes, inter alia.

In accordance with certain preferred embodiments of this aspect of the invention, there are provided products, compositions and methods, inter alia, for, among other things: assessing ICE LAP-6 expression in cells by determining ICE LAP-6 polypeptides or ICE LAP-6-encoding mRNA; as an antiviral agent, an anti-tumor agent and to control embryonic development and tissue homeostasis in vitro, ex vivo or in vivo by exposing cells to ICE LAP-6 polypeptides or polynucleotides as disclosed herein; assaying genetic variation and aberrations, such as defects, in ICE LAP-6 genes; and administering an ICE LAP-6 polypeptide or polynucleotide to an organism to augment ICE LAP-6 function or remediate ICE LAP-6 dysfunction. Agonists targeted to defective cellular proliferation, including, for example, cancer cell and solid tumor cell proliferation, may be used for the treatment of these diseases. Such targeting may be achieved via gene therapy using antibody fusions. Agonists may also be used to treat follicular lymphomas, carcinomas associated with p53 mutations, autoimmune disorders, such as, for example, SLE, immune-mediated glomerulonephritis; and hormone-dependent tumors, such as, for example, breast cancer, prostate cancer and ovary cancer, and viral infections, such as, for example, herpesviruses, poxviruses and adenoviruses.

In accordance with certain preferred embodiments of this and other aspects of the invention there are provided probes that hybridize to human ICE LAP-6 sequences.

In certain additional preferred embodiments of this aspect of the invention there are provided antibodies against ICE LAP-6 polypeptides. In certain particularly preferred embodiments in this regard, the antibodies are highly selective for human ICE LAP-6.

In accordance with another aspect of the present invention, there are provided ICE LAP-6 agonists. Among preferred agonists are molecules that mimic ICE LAP-6, that bind to ICE LAP-6-binding molecules or receptor molecules, and that elicit or augment ICE LAP-6-induced responses. Also among preferred agonists are molecules that interact with ICE LAP-6 or ICE LAP-6 polypeptides, or with other modulators of ICE LAP-6 activities and/or gene expression, and thereby potentiate or augment an effect of ICE LAP-6 or more than one effect of ICE LAP-6.

In accordance with yet another aspect of the present invention, there are provided ICE LAP-6 antagonists. Among preferred antagonists are those which mimic ICE LAP-6 so as to bind to ICE LAP-6 receptor or binding molecules but not elicit an ICE LAP-6-induced response or more than one ICE LAP-6-induced response. Also among preferred antagonists are molecules that bind to or interact with ICE LAP-6 so as to inhibit an effect of ICE LAP-6 or more than one effect of ICE LAP-6 or which prevent expression of ICE LAP-6.

In a further aspect of the invention there are provided compositions comprising an ICE LAP-6 polynucleotide or an ICE LAP-6 polypeptide for administration to cells in vitro, to cells ex vivo and to cells in vivo, or to a multicellular organism. In certain particularly preferred embodiments of this aspect of the invention, the compositions comprise an ICE LAP-6 polynucleotide for expression of an ICE LAP-6 polypeptide in a host organism for treatment of disease. Particularly preferred in this regard is expression in a human patient for treatment of a dysfunction associated with aberrant endogenous activity of ICE LAP-6.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 [SEQUENCE ID NO. 1] shows the predicted amino acid sequence of human ICE LAP-6. The active site pentapeptide QACGG (SEQ ID NO:11) is underlined. Putative amino acid (Asp) cleavage sites are indicated with bold letters.

FIGS. 2A–2C [SEQUENCE ID NO. 2] show a nucleic acid sequence of human ICE LAP-6.

FIG. 3 [SEQUENCE ID NO. 3] shows a nucleic acid sequence variant derived from human ICE LAP-6.

FIG. 4 [SEQUENCE ID NO. 4] shows an amino acid sequence variant derived from human ICE LAP-6.

GLOSSARY

Figure 5:
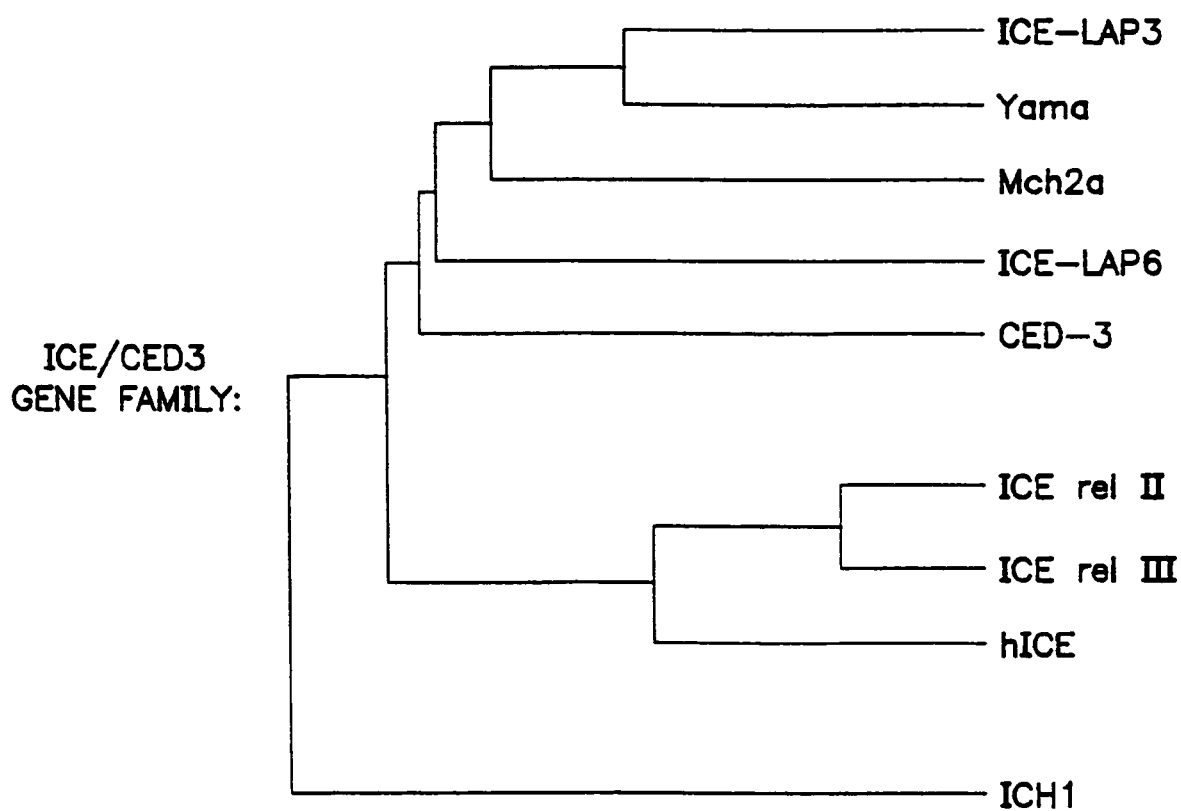
FIG. 5 shows phylogenetic analysis of the ICE/ced-3 gene family.

The following illustrative explanations are provided to facilitate understanding of certain terms used frequently herein, particularly in the examples. The explanations are provided as a convenience and are not limitative of the invention.

DIGESTION of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 µg of plasmid or DNA fragment is digested with about 2 units of enzyme in about 20 µl of reaction buffer. For the purpose of isolating DNA fragments for plasmid construction, typically 5 to 50 µg of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

GENETIC ELEMENT generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

IDENTITY or SIMILARITY, as known in the art, are relationships between two polypeptides as determined by comparing the amino acid sequence and its conserved amino acid substitutes of one polypeptide to the sequence of a second polypeptide. Moreover, also known in the art is "identity" which means the degree of sequence relatedness between two polypeptide or two polynucleotides sequences as determined by the identity of the match between two strings of such sequences. Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity and similarity between two polynucleotide or polypeptide sequences, the terms "identity" and "similarity" are well known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods commonly employed to determine identity or similarity between two sequences include, but are not limited to disclosed in Carillo, H., and Lipman, D., SLAM *J. Applied Math.*, 48: 1073 (1988). Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, J., et al., *Nucleic Acids Research* 12 (1): 387 (1984)), BLASTP, BLASTN, FASTA (Atschul, S. F. et al., *J. Molec. Biol.* 215: 403 (1990)).

ISOLATED means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., *MOLECULAR CLONING, A LABORATORY MANUAL*, 2nd Ed.; Cold Spring Harbor Laboratory Press, Cold Spring Harbor, N.Y. (1989) ("Sambrook") and Maniatis et al., pg. 146, as cited below.

OLIGONUCLEOTIDE(S) refers to relatively short polynucleotides. Often the term refers to single-stranded deoxyribonucleotides, but it can refer as well to single-or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

PLASMIDS generally are designated herein by a lower case p preceded and/or followed by capital letters and/or numbers, in accordance with standard naming conventions that are familiar to those of skill in the art.

Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *PROTEINS—STRUCTURE AND MOLECULAR PROPERTIES*, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in *POSTTRANSLATIONAL COVALENT MODIFICATION OF PROTEINS*, B. C. Johnson, Ed., Academic Press, New York (1983); Seifter et al., Analysis for protein modifications and nonprotein cofactors, Meth. Enzymol. 182: 626–646 (1990) and Rattan et al., *Protein Synthesis: Posttranslational Modifications and Aging*, Ann. N.Y. Acad. Sci. 663: 48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cell often carry out the same post-translational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

RECEPTOR MOLECULE, as used herein, refers to molecules which bind or interact specifically with ICE LAP6 polypeptides of the present invention, including not only classic receptors, which are preferred, but also other molecules that specifically bind to or interact with polypeptides of the invention (which also may be referred to as "binding molecules" and "interaction molecules," respectively and as "ICE LAP-6 binding molecules" and "ICE LAP-6 interaction molecules." Binding between polypeptides of the invention and such molecules, including receptor or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention.

Receptors also may be non-naturally occurring, such as antibodies and antibody-derived reagents that bind specifically to polypeptides of the invention.

DESCRIPTION OF THE INVENTION

The present invention relates to novel ICE LAP-6 polypeptides and polynucleotides, among other things, as described in greater detail below. In particular, the invention relates to polypeptides and polynucleotides of a novel human ICE LAP-6, which is related by amino acid sequence homology to human interleukin-1 beta converting enzyme apoptosis protease polypeptides. The invention relates especially to ICE LAP-6 having the nucleotide and amino acid sequences set out in FIGS. 1 and 2A–2C respectively. It will be appreciated that the nucleotide and amino acid sequences set out in FIGS. 2A–2C and 1 respectively, were obtained by sequencing the cDNA obtained from a human K562 (erythroleukemia) cell line cDNA library.

Polynucleotides

In accordance with one aspect of the present invention, there are provided isolated polynucleotides which encode the ICE LAP-6 polypeptide having the deduced amino acid sequence of FIG. 1 or the polypeptide encoded by the deposited clone.

In accordance with another aspect of the present invention, there are provided isolated polynucleotides which encode the ICE LAP-6 polypeptide having the deduced amino acid sequence of FIG. 1 or the polypeptide encoded by the deposited clone.

Using the information provided herein, such as the polynucleotide primer sequences set out in Example 1, a polynucleotide of the present invention encoding human ICE LAP-6 polypeptide may be obtained using standard cloning and screening procedures, such as those for cloning cDNAs using mRNA from cells from human neutrophils and kidney tissue as starting material. Illustrative of the invention, the polynucleotide of the invention was discovered as described in Example 1. ICE LAP 7 can also be obtained from other tissues and cDNA libraries, for example, libraries derived from cells of human cells, tissue and cell lines such as, activated human neutrophil, erythroleukemia and kidney cells.

Human ICE LAP-6 of the invention is structurally related to other proteins of the human interleukin-1 beta converting enzyme apoptosis protease family, as shown by the results of sequencing the cDNA encoding human ICE LAP-6 in FIG. 1. The cDNA of FIGS. 2A–2C was obtained as described in Example 1. The polyp eptide of FIG. 1 and the polypeptide encoded by the deposited clone each are proteins which have a deduced molecular weight of about 45.8 kDa.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide derived using the primers set forth in Example 1, or the polynucleotide of FIGS. 2A–2C. It also may be a polynucleotide with a different sequence, which, as a result of the redundancy (degeneracy) of the genetic code, encodes the polypeptide of the cDNA of FIG. 1 or the polypeptide encoded by the deposited clone.

Polynucleotides of the present invention which encode the polypeptide of FIG. 1 or the polypeptide encoded by the deposited clone may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the pQE vector (Qiagen, Inc.), among others, many of which are commercially available. As described in Gentz et al., *Proc. Natl. Acad. Sci.*, USA 86: 821–824 (1989), for instance, hexa-histidine provides for convenient purification of the fusion protein. The HA tag corresponds to an epitope derived of influenza hemagglutinin protein, which has been described by Wilson et al., *Cell* 37: 767 (1984), for instance.

Also provided is mature ICE LAP-6 processed from its precursor molecule, via autocatalysis or by other enzymes, to produce two subunits, which form an active heterodimer (both subunits) or tetramer (two sets of such heterodimers).

In accordance with the foregoing, the term "polynucleotide encoding a polypeptide" as used herein encompasses polynucleotides which include a sequence encoding a polypeptide of the present invention, particularly the human ICE LAP-6 having the amino acid sequence set out in FIG. 1 or the amino acid sequence of the polypeptide encoded by the deposited clone. The term encompasses polynucleotides that include a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the polypeptide having the deduced amino acid sequence of FIG. 1 or the amino acid sequence of the polypeptide encoded by the deposited clone. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of ICE LAP-6 set out in FIG. 1 or the amino acid sequence of the polypeptide encoded by the deposited clone; variants, analogs, derivatives and fragments thereof, and fragments of the variants, analogs and derivatives.

Further particularly preferred in this regard are polynucleotides encoding ICE LAP-6 variants, analogs, derivatives and fragments, and variants, analogs and derivatives of the fragments, which have the amino acid sequence of the ICE LAP-6 polypeptide of FIG. 1 or the polypeptide encoded by the deposited clone in which several, a few, 5 to 10, 1 to 5, 1 to 3, 2, 1 or no amino acid residues are substituted, deleted or added, in any combination. Especially preferred among these are substitutions, additions and deletions, which do not alter the properties and activities of the ICE LAP-6. Also especially preferred in this regard are conservative substitutions. Most highly preferred are polynucleotides encoding polypeptides having the amino acid sequence of FIG. 1 or the amino acid sequence of the polypeptide encoded by the deposited clone, without substitutions.

Further preferred embodiments of the invention are polynucleotides that are at least 70% identical to a polynucleotide encoding the ICE LAP-6 polypeptide having the amino acid sequence set out in FIG. 1 or the amino acid sequence of the polypeptide encoded by the deposited clone, and polynucleotides which are complementary to such polynucleotides. Alternatively, most highly preferred are polynucleotides that comprise a region that is at least 80% identical to a polynucleotide encoding the ICE LAP-6 polypeptide of the human cDNA and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiments in this respect, moreover, are polynucleotides which encode polypeptides which retain substantially the same biological function or activity as the mature polypeptide encoded by the cDNA of FIGS. 2A–2C encoded by the polynucleotide sequence of the deposited clone, or derived using the primers set forth in Example 1.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for cDNA and genomic DNA to isolate full-length cDNAs and genomic clones encoding ICE LAP-6 and to isolate cDNA and genomic clones of other genes that have a high sequence similarity to the human ICE LAP-6 gene. Such probes generally will comprise at least 15 bases. Preferably, such probes will have at least 30 bases and may have at least 50 bases. Particularly preferred probes will have at least 30 bases and will have 50 bases or less.

For example, the coding region of the ICE LAP-6 gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease, as further discussed herein relating to polynucleotide assays, inter alia.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited Materials

A deposit containing a human ICE LAP-6 cDNA has been deposited with the American Type Culture Collection, as noted above. Also as noted above, the human cDNA deposit is referred to herein as "the deposited clone" or as "the cDNA of the deposited clone."

The deposited clone was deposited with the American Type Culture Collection, (ATCC™), 10801 University Boulevard, Manassas, Va. 20110-2209.

The deposited material is a pBluescript SK (−) plasmid (Stratagene, La Jolla, Calif.) that contains the full length ICE LAP-6 cDNA, referred to as "1095150" upon deposit and assigned ATCC™ Deposit Number 97590.

The deposit has been made under the terms of the Budapest Treaty on the international recognition of the deposit of microorganisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. § 112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a human ICE LAP-6 polypeptide which has the deduced amino acid sequence of FIG. 1 and the amino acid sequence of the the polypeptide encoded by the deposited clone.

The invention also relates to fragments, analogs and derivatives of these polypeptides. The terms "fragment," "derivative" and "analog" when referring to the polypeptide of FIG. 1 or the polypeptide encoded by the deposited clone, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIG. 1 or the polypeptide encoded by the deposited clone each may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of ICE LAP-6 set out in FIG. 1 or the amino acid sequence of the polypeptide encoded by the deposited clone, variants, analogs, derivatives and fragments thereof, and variants, analogs and derivatives of the fragments. Alternatively, particularly preferred embodiments of the invention in this regard are polypeptides having the amino acid sequence of the ICE LAP-6, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the ICE LAP-6 polypeptide of FIG. 1 or the amino acid sequence of the polypeptide encoded by the deposited clone, in which several, a few, 5 to 10, 1 to 5, 1 to 3, 2, 1 or no amino acid residues are substituted, deleted or added, in any combination. Especially preferred among these are substitutions, additions and deletions, which do not alter the properties and activities of the ICE LAP-6. Also especially preferred in this regard are conservative substitutions. Most highly preferred are polypeptides having the amino acid sequence of FIG. 1 or the amino acid sequence of the polypeptide encoded by the deposited clone without substitutions.

The polypeptides and polynucleotides of the present invention are preferably provided in an isolated form, and preferably are purified to homogeneity.

The polypeptides of the present invention include the polypeptide of FIG. 1 or the polypeptide encoded by the deposited clone (in particular the mature polypeptide) as well as polypeptides which have at least 80% identity to the polypeptide of FIG. 1 or the polypeptide encoded by the deposited clone and more preferably at least 90% similarity (more preferably at least 90% identity) to the polypeptide of FIG. 1 or the polypeptide encoded by the deposited clone and still more preferably at least 95% similarity (still more preferably at least 95% identity) to the polypeptide of FIG. 1 or the polypeptide encoded by the deposited clone and also include portions of such polypeptides with such portion of the polypeptide generally containing at least 30 amino acids and more preferably at least 50 amino acids.

Fragments or portions of the polypeptides of, the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of ICE LAP-6, most particularly fragments of the ICE LAP-6 having the amino acid set out in FIG. 1 or the amino acid sequence of the polypeptide encoded by the deposited clone, and fragments of variants and derivatives of the ICE LAP-6 of FIG. 1 or the polypeptide encoded by the deposited clone, such as, for example the amino acid sequence of FIG. 4.

In this regard a fragment is a polypeptide having an amino acid sequence that entirely is, the same as part but not all of the amino acid sequence of the aforementioned ICE LAP-6 polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of an ICE LAP-6 polypeptide of the present comprised within a precursor polypeptide designed for expression in a host and having heterologous pre and pro-polypeptide regions fused to the amino terminus of the ICE LAP-6 fragment and an additional region fused to the carboxyl terminus of the fragment. Therefore, fragments in one aspect of the meaning intended herein, refers to the portion or portions of a fusion polypeptide or fusion protein derived from ICE LAP-6.

As representative examples of polypeptide fragments of the invention, there may be mentioned those which have from about 5–15, 10–20, 15–40, 30–55, 41–65, 41–80, 41–90, 50–100, 75–100, 90–115, 100–125, and 110–113 amino acids long.

In this context about includes the particularly recited range and ranges larger or smaller by several, a few, 5, 4, 3, 2 or 1 amino acid at either extreme or at both extremes. For instance, about 40–90 amino acids in this context means a polypeptide fragment of 40 plus or minus several, a few, 5, 4, 3, 2 or 1 amino acids to 90 plus or minus several a few, 5, 4, 3, 2 or 1 amino acid residues, i.e., ranges as broad as 40 minus several amino acids to 90 plus several amino acids to as narrow as 40 plus several amino acids to 90 minus several amino acids.

Highly preferred in this regard are the recited ranges plus or minus as many as amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 5–15, 10–20, 15–40, 30–55, 41–65, 41–80, 41–90, 50–100, 75–100, 90–115, 100–125, and 110–113 amino acids long.

Among especially preferred fragments of the invention are truncation mutants of ICE LAP-6. Truncation mutants include ICE LAP-6 polypeptides having the amino acid sequence of FIG. 1 or the amino acid sequence of the polypeptide encoded by the deposited clone, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally.

Also preferred in this aspect of the invention are fragments characterized by structural or functional attributes of ICE LAP-6. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of ICE LAP-6.

Among highly preferred fragments in this regard are those that comprise regions of ICE LAP-6 that combine several structural features, such as several of the features set out above. In this regard, the regions defined by the residues about 10 to about 20, about 40 to about 50, about 70 to about 90 and about 100 to about 113 of FIG. 1 or the polypeptide encoded by the deposited clone, which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of ICE LAP-6. Most highly preferred in this regard are fragments that have a chemical, biological or other activity of ICE LAP-6, including those with a similar activity or an improved activity, or with a decreased undesirable activity. Highly preferred in this regard are fragments that contain regions that are homologs in sequence, or in position, or in both sequence and to active regions of related polypeptides, such as the related polypeptides set out in FIGS. 2A–2C, which include human interleukin-1 beta converting enzyme apoptosis proteases. Among particularly preferred fragments in these regards are truncation mutants, as discussed above.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above. Preferred polynucleotides fragments may be derived from the sequences of FIGS. 2A–2C.

Vectors, Host Cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as simian virus 40 ("SV40"), vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region; a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Hosts for a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia Among preferred eukaryotic vectors are pWLNEO, pSV2CAT, pOG44, pXT1 and pSG available from Suatagene; and pSVY3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the *E. coli* lacI and lacZ promoters, the T3 and T7 promoters, the gpt promoter, the lambda PR. PL promoters and the trp promoter.

Among known eukaryotic promoters suitable in this regard are the cytomegalovirus ("CMV") immediate early promoter, the HSV thymidine kinase promoter, the early and late SV40 promoters, the promoters of retroviral LTRs, such as those of the Rous sarcoma virus ("RoSV"), and metal-lothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as SAMBROOK.

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., cited above.

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of *E. coli* and the trp1 gene of *S. cerevisiae*.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, a region may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include *Escherichia coli, Bacillus subtilis* and *Salmonella typhimurium*. Various species of *Pseudomonas, Streptomyces*, and *Staphylococcus* are suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. Examples of mammalian expression systems include the COS-6 lines of monkey kidney fibroblast, described in Gluzman et al., Cell 23: 175 (1981). Other cell lines capable of expressing a compatible vector include for example, the C127, 3T3, CHO, HeLa, human kidney 293 and BHK cell lines.

Mammalian expression vectors will comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

The ICE LAP-6 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

ICE LAP-6 polynucleotides and polypeptides may be used in accordance with the present invention for a variety of applications, particularly those that make use of the chemical and biological properties of ICE LAP-6. Additional applications relate to diagnosis and to treatment of disorders of cells, tissues and organisms. These aspects of the invention are illustrated further by the following discussion.

Polynucleotide Assays

This invention is also related to the use of the ICE LAP-6 polynucleotides to detect complementary polynucleotides such as, for example, as a diagnostic reagent. Detection of a mutated form of ICE LAP-6 associated with a dysfunction will provide a diagnostic tool that can add or define a diagnosis of a disease or susceptibility to a disease which results from under-expression over-expression or altered expression of ICE LAP-6. Individuals carrying mutations in the human ICE LAP-6 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. PCR (Saiki et al., Nature, 324: 163–166 (1986)). RNA or cDNA may also be used in the same ways. As an example, PCR primers complementary to the nucleic acid encoding ICE LAP-6 can be used to identify and analyze ICE LAP6 expression and mutations. For example, deletions and insertions can be detected by a change in size of the amplified product in comparison to the normal genotype. Point mutations can be identified by hybridizing amplified DNA to radiolabeled ICE LAPS RNA or alternatively, radiolabeled ICE LAP-6 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230: 1242 (1985)).

Sequence changes at specific locations also may be revealed by nuclease protection assays, such as RNase and S1 protection or the chemical cleavage method (e.g., Cotton et al., Proc. Natl. Acad. Sci., USA, 85: 4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

In accordance with a further aspect of the invention, there is provided a process for determining disease associated with viral infection, tumorogenesis and to control embryogenesis and tissue homeostasis. Diseases associated with viral infection, tumorogenesis and to control embryogenesis and tissue homeostasis, or a susceptibility to viral infection, tumorogenesis and to diseases and defects in the control of control of embryogenesis and tissue homeostasis. Thus, a mutation in ICE LAP-6 indicates a susceptibility to viral infection, tumorogenesis and to diseases and defects in the control embryogenesis and tissue homeostasis, and the nucleic acid sequences described above may be employed in an assay for ascertaining such susceptibility. Thus, for example, the assay may be employed to determine a mutation in a human ICE LAP-6 protein as herein described, such as a deletion, truncation, insertion, frame shift, etc., with such mutation being indicative of a susceptibility to viral infection, tumorogenesis and to diseases and defects in the control of embryogenesis and tissue homeostasis.

A mutation may be ascertained for example, by a DNA sequencing assay. Tissue samples, including but not limited to blood samples are obtained from a human patient The samples are processed by methods known in the art to capture the RNA. First strand cDNA is synthesized from the RNA samples by adding an oligonucleotide primer consisting of polythymidine residues which hybridize to the polyadenosine stretch present on the mRNA's. Reverse transcriptase and deoxynucleotides are added to allow synthesis of the first strand cDNA. Primer sequences are synthesized based on the DNA sequence of the ICE LAP-6 protein of the invention. The primer sequence is generally comprised of at least 15 consecutive bases, and may contain at least 30 or even 50 consecutive bases.

Individuals carrying mutations in the gene of the present invention may also be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., *Nature*, 324:163–166 (1986)) prior to analysis. RT-PCR can also be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding ICE LAP-6 can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Primers, selected by well known methods, may be used for amplifying ICE LAP-6 cDNA isolated from a sample derived from a patient. The invention also provides the primers selected with 1, 2, 3 or 4 nucleotides removed from the 5' and/or the 3' end. The primers may be used to amplify the gene isolated from the patient such that the gene may then be subject to various techniques for elucidation of the DNA sequence. In this way, mutations in the DNA sequence may be diagnosed.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different-sequences may be distinguished on denaturing formamide gradient gels in which the mobilities of different DNA fragments are retarded in the gel at different positions according to their specific melting or partial melting temperatures (see, e.g., Myers et al., *Science*, 230:1242 (1985)).

Sequence changes at specific locations may also be revealed by nuclease protection assays, such as RNase and S1 protection or the chemical cleavage method (e.g., Cotton et al., *PNAS, USA*, 85:4397–4401 (1985)).

Thus, the detection of a specific DNA sequence and/or quantitation of the level of the sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

The, invention provides a process for diagnosing or detecting, disease, particularly Alzheimer's disease, Parkinson's disease, rheumatoid arthritis, septic shock, sepsis, stroke, chronic inflammation, acute inflammation, CNS inflammation, osteoporosis, ischemia reperfusion injury, cell death associated with cardiovascular disease, polycystic kidney disease, apoptosis of endothelial cells in cardiovascular disease, degenerative liver disease, MS, ALS, cererbellar degeneration, ischemic injury, myocardial infarction, AIDS, myelodysplastic syndromes, aplastic anemia, male pattern baldness, and head injury damage, as well as a susceptibility to viral infection and cancer, an to detect aberrant control of embryonic development and tissue homeostasis, comprising determining from a sample derived from a patient altered expression of polynucleotide having the sequence of FIG. 1 or the polynucleotide sequence of the deposited clone as compared to normal control samples. Expression of polynucleotide can be measured using any one of the methods well known in the art for the quantation of polynucleotides, such as, for example, PCR, RT-PCR, RNase protection, Northern blotting and other hybridization methods.

In addition to more conventional gel-electrophoresis and DNA sequencing, mutations can also be detected by in situ analysis.

Fluorescence in situ hybridization (FISH) of a cDNA clone to a metaphase chromosomal spread can be used to provide a precise chromosomal location.

As an example of how this is performed, ICE LAP6 DNA is digested and purified with QLAEX II DNA purification kit (QIAGEN, Inc., Chatsworth, Calif.) and ligated to Super Cos1 cosmid vector (STRATAGENE, La Jolla, Calif.). DNA is purified using Qiagen Plasmid Purification Kit (QIAGEN Inc., Chatsworth, Calif.) and 1 mg is labeled by nick translation in the presence of Biotin-dATP using BioNick Labeling Kit (GibcoBRL, Life Technologies Inc., Gaithersburg, Md.). Biotinilation is detected with GENE-TECT Detection System (CLONTECH Laboratories, Inc. Palo Alto, Calif.). In situ Hybridization is performed on slides using ONCOR Light Hybridization Kit (ONCOR, Gaithersberg, Md.) to detect single copy sequences on metaphase chromosomes. Peripheral blood of normal donors is cultured for three days in RPMI 1640 supplemented with 20% FCS, 3% PHA and penicillin/streptomycin, synchronized with $10^{-6}$ M methotrexate for 17 hours and washed twice with unsupplemented RPME Cells are incubated with $10^{-3}$ M thymidine for 7 hours. The cells are arrested in metaphase after 20 minutes incubation with colcemid (0.5 µg/ml) followed by hypotonic lysis in 75 mM KCl for 15 minutes at 37° C. Cell pellets are then spun out and fixed in Carnoy's fixative (3:1 methanol/acetic acid).

Metaphase spreads are prepared by adding a drop of the suspension onto slides and aid dried. Hybridization is performed by adding 100 ng of probe suspended in 10 ml of hybridization mix (50% formamide, 2×SSC, 1% dextran sulfate) with blocking human placental DNA 1 µg/ml), Probe mixture is denatured for 10 minutes in 70° C. water bath and incubated for 1 hour at 37° C., before placing on a prewarmed (37° C.) slide, which is previously denatured in 70% formamide/2×SSC at 70° C., and dehydrated in ethanol series, chilled to 4° C.

Slides are incubated for 16 hours at 37° C. in a humidified chamber. Slides are washed in 50% formamide/2×SSC for 10 minutes at 41° C. and 2×SSC for 7 minutes at 37° C. Hybridization probe is detected by incubation of the slides with FTIC-Avidin (ONCOR, Gaithersberg, Md.), according to the manufacturer protocol. Chromosomes are counterstained with propridium iodine suspended in mounting medium Slides are visualized using a Leitz ORTHOPLAN 2-epifluorescence microscope and five computer images are taken using Imagenetics Computer and MacIntosh printer.

Once a sequence has been mapped to a precise chromosomal location, the physical position of the sequence on the chromosome can be correlated with genetic map data. Such data are found, for example, in V. McKusick, *Mendelian Inheritance in Man* (publicly available on-line via computer (Internet)). The relationship between genes and diseases that have been mapped to the same chromosomal region are then identified through linkage analysis using well known methods.

Unless otherwise stated, transformation was performed as described in the method of Graham, F. and Van der Eb, A., *Virology*, 52:456–457 (1973).

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of an ICE LAP-6 gene. This can be accomplished using a variety of well known techniques and libraries, which generally are available commercially. The genomic DNA is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with cDNA as short as 50 or 60. For a review of this technique, see Verma et al., *HUMAN CHROMOSOMES: A MANUAL OF BASIC TECHNIQUES*, Pergamon Press, New York (1988).

Once a sequence has been mapped to a precise chromosomal location, the physical position of the sequence on the chromosome can be correlated with genetic map data Such data are found, for example, in V. McKusick, *MENDELIAN INHERITANCE IN MAN* (publicly available on line via computer). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Polypeptide Assays

The present invention also relates to a quantitative and semi-quantitative diagnostic assays for detecting levels of ICE LAP-6 protein in cells and tissues, including determination of normal and abnormal levels. Thus, for instance, a diagnostic assay in accordance with the invention for detecting over-expression of ICE LAP-6 protein compared to normal control tissue samples may be used to detect the presence of a tumor, or other abnormal cell growth or proliferation, for example. Assay techniques that can be used to determine levels of a protein, such as an ICE LAP-6 protein of the present invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to ICE LAP-6, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any ICE LAP-6 proteins attached to the polystyrene dish Unbound monoclonal antibody is washed out with buffer. The reporter antibody linked to horseradish peroxidase is placed in the dish resulting in binding of the reporter antibody to any monoclonal antibody bound to ICE LAP-6. Unattached reporter antibody is then washed out Reagents for peroxidase activity, including a colorimetric substrate are then added to the dish Immobilized peroxidase, linked to ICE LAP-6 through the primary and secondary antibodies, produces a colored reaction product. The amount of color developed in a given time period indicates the amount of ICE LAP-6 protein present in the sample. Quantitative results typically are obtained by reference to a standard curve.

A competition assay may be employed wherein antibodies specific to ICE LAP-6 attached to a solid support and labeled ICE LAP-6 and a sample derived from the host are passed over the solid support and the amount of label detected attached to the solid support can be correlated to a quantity of ICE LAP-6 in the sample.

Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., *Nature* 256: 495–497 (1975), the trioma technique, the human B-cell hybridoma technique (Kozbor et al., *Immunology Today* 4: 72 (1983) and the EBV-hybridoma technique to produce human monoclonal antibodies (Cole et al., pg. 77–96 in *MONOCLONAL ANTIBODIES AND CANCER THERAPY*, Alan R Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Thus, among others, antibodies against ICE LAP-6 may be employed to inhibit the action of such ICE LAP-6 polypeptides, for example, in the treatment of Alzheimer's disease, Parkinson's disease, rheumatoid arthritis, septic shock, sepsis, stroke, chronic inflammation, acute inflammation, CNS inflammation, osteoporosis, ischemia reperfusion injury, cell death associated with cardiovascular disease, polycystic kidney disease, apoptosis of endothelial cells in cardiovascular disease, degenerative liver disease, MS, ALS, cererbellar degeneration, ischemic injury, myocardial infarction, ASS, myelodysplastic syndromes, aplastic anemia, male pattern baldness, and head injury damage.

ICE LAP-6 Binding Molecules and Assays

This invention also provides a method for identification of molecules, such as receptor molecules, that bind ICE LAP-6. Genes encoding proteins that bind ICE LAP-6, such as receptor proteins, can be identified by numerous methods known to those of skill in the art, for example, ligand panning and FACS sorting. Such methods are described in many laboratory manuals such as, for instance, Coligan et al., *Current Protocols in Immunology* 1(2): Chapter 5 (1991).

For instance, expression cloning may be employed for this purpose. To this end polyadenylated RNA is prepared from a cell responsive to ICE LAP-6, a cDNA library is created from this RNA, the library is divided into pools and the pools are transfected individually into cells that are not responsive to ICE LAP-6. The transfected cells then are exposed to labeled ICE LAP-6. (ICE LAP-6 can be labeled by a variety of well-known techniques including standard methods of radio-iodination or inclusion of a recognition site for a site-specific protein kinase.) Following exposure, the cells are fixed and binding of ICE LAP-6 is determined. These procedures conveniently are carried out on glass slides.

Pools are identified of cDNA that produced ICE LAP-6-binding cells. Sub-pools are prepared from these positives, transfected into host cells and screened as described above. Using an iterative sub-pooling and re-screening process, one or more single clones that encode the putative binding molecule, such as a receptor molecule, can be isolated.

Alternatively a labeled ligand can be photoaffinity linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to assess ICE LAP-6 binding capacity of ICE LAP-6 binding molecules, such as receptor molecules, in cells or in cell-free preparations.

Agonists and Antagonists—Assays and Molecules

The invention also provides a method of screening compounds to identify those which enhance or block the action of ICE LAP-6 on cells, such as its interaction with ICE LAP-6-binding molecules such as receptor molecules. An agonist is a compound which increases the natural biological functions of ICE LAP-6 or which functions in a manner similar to ICE LAP-6, while antagonists decrease or eliminate such functions.

For example, a cellular compartment, such as a membrane or a preparation thereof, such as a membrane-preparation, may be prepared from a cell that expresses a molecule that binds ICE LAP-6, such as a molecule of a signaling or regulatory pathway modulated by ICE LAP-6. The preparation is incubated with labeled ICE LAP-6 in the absence or the presence of a candidate molecule which may be an ICE LAP-6 agonist or antagonist. The ability of the candidate molecule to bind the binding molecule is reflected in decreased binding of the labeled ligand. Molecules which bind gratuitously, i.e., without inducing the effects of ICE LAP-6 on binding the ICE LAP-6 binding molecule, are most Likely to be good antagonists. Molecules that bind well and elicit effects that are the same as or closely related to ICE LAP-6 are agonists.

ICE LAP-6 like effects of potential agonists and antagonists may by measured, for instance, by determining activity of a second messenger system following interaction of the candidate molecule with a cell or appropriate cell preparation, and comparing the effect with that of ICE LAP-6 or molecules that elicit the same effects as ICE LAP-6. Second messenger systems that may be useful in this regard include but are not limited to AMP guanylate cyclase, ion channel or phosphoinositide hydrolysis second messenger systems.

Another example of an assay for ICE LAP-6 antagonists is a competitive assay that combines ICE LAP-6 and a potential antagonist with membrane-bound ICE LAP-6 receptor molecules or recombinant ICE LAP-6 receptor molecules under appropriate conditions for a competitive inhibition assay. ICE LAP-6 can be labeled, such as by radioactivity, such that the number of ICE LAP-6 molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing ICE LAP-6-induced activities, thereby preventing the action of ICE LAP-6 by excluding ICE LAPS from binding.

Potential antagonists include a small molecule which binds to and occupies the binding site of the polypeptide thereby preventing binding to cellular binding molecules, such as receptor molecules, such that normal biological activity is prevented. Examples of small molecules include but are not limited to small organic molecules, peptides or peptide-like molecules. Antoher antagonist is an oligopeptide comprising the cleavage site recognition motif for ICE LAP-6.

Other potential antagonists include antisense molecules. Antisense technology can be used to control gene expression through antisense DNA or RNA or through triple-helix formation. Antisense techniques are discussed, for example, in—Okano, J. Neurochem. 56: 560 (1991); *OLIGODEOXY-NUCLEOTIDES AS ANTISENSE INHIBITORS OF GENE EXPRESSION*, CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan et al., *Science* 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide from about 10 to 40 base pairs in length. A DNA oligonucleotide is designed to be complementary to a region of the gene involved in transcription thereby preventing transcription and the production of ICE LAP-6. The antisense RNA oligonucleotide hybridizes to the mRNA in vivo and blocks translation of the mRNA molecule into ICE LAP-6 polypeptide. The oligonucleotides described above can also be delivered to cells such that the antisense RNA or DNA may be expressed in vivo to inhibit production of ICE LAP-6.

Agonists targeted to defective cellular proliferation, including, for example, cancer cells and solid tumor cells may be used for the treatment of these diseases. Such targeting may be achieved via gene therapy of using antibody fusions.

Agonists may also be used to treat follicular lymphomas, carcinomas associated with p53 mutations, autoimmune disorders, such as, for example, SLE, immune-mediated glomerulonephritis; and hormone-dependent tumors, such as, for example, breast cancer, prostate cancer and ovary cancer, and viral infections, such as, for example, herpesviruses, poxviruses and adenoviruses.

The antagonists may be employed in a composition with a pharmaceutically acceptable carrier, e.g., as hereinafter described.

The antagonists may be employed for instance to inhibit the action of ICE LAP-6 polypeptides, for example, in the treatment of Alzheimer's disease, Parkinson's disease, rheumatoid arthritis, septic shock, sepsis, stroke, chronic inflammation, acute inflammation, CNS inflammation, osteoporosis, ischemia reperfusion injury, cell death associated with cardiovascular disease, polycystic kidney disease, apoptosis of endothelial cells in cardiovascular disease, degenerative liver disease, MS, ALS, cererbellar degeneration, ischemic injury, myocardial infarction, AIDS, myelodysplastic syndromes, aplastic anemia, male pattern baldness, and head injury damage.

The antagonists may be employed in a composition with a pharmaceutically acceptable carrier, e.g., as hereinafter described.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 μg/kg body weight. In most cases they will be administered in an amount not in excess of about 8 mg/kg body weight per day. Preferably, in most cases, dose is from about 10 μg/kg to about 1 mg/kg body weight, daily. It will be appreciated that optimum dosage will be determined by standard methods for each treatment modality and indication, taking into account the indication, its severity, route of administration, complicating conditions and the like.

Gene Therapy

The ICE LAP-6 polynucleotides, polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter, and the CMV promoter described in Miller et al., *Biotechniques* 7: 980–990 (1989), or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter, or heterologous promoters, such as the CMV promoter, the respiratory syncytial virus ("RSV") promoter, inducible promoters, such as the MMT promoter, the metallothionein promoter, heat shock promoters; the albumin promoter, the ApoAI promoter, human globin promoters; viral thymidine kinase promoters, such as the Herpes Simplex thymidine kinase promoter, retroviral LTRs (including the modified retroviral LTRs herein above described); the β-actin promoter, and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Ψ-2, Ψ-AM, PA12, T19-14X VT-19 17-H2, YCRE, YCREP, GP+E-86, GP+envAm12, and DAN cell lines as described in Miller, A., *Human Gene Therapy* 1: 5–14 (1990). The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., cited above.

All parts or amounts set out in the following examples are by weight, unless otherwise specified. As used herein, "CTLs" means cytotoxic lymphocytes.

Unless otherwise stated, size separation of fragments in the examples below was carried out using standard techniques of agarose and polyacrylamide gel electrophoresis ("PAGE") in Sambrook and numerous other references such as, for instance, by Goeddel et al., *Nucleic Acids Res.* 8: 4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 µg of DNA.

Example 1

Cloning, Expression and Purification of Human ICE LAP-6

SUMMARY

Members of the ICE/ced-3 gene family are belived to be effector components of the cell death machinery. Herein this Example, a novel member of this family designated ICE LAP-6 is characterized. By phylogenetic analysis, ICE LAP-6 is classified into the Ced-3 subfamily which includes Ced-3, Yama/CPP32/apopain, Mch2 and ICE LAP-3/Mch3/CMH-1. ICE LAP-6 contains an active site QACGG (SEQ ID NO:11) pentapeptide, rather than the QACRG (SEQ ID NO:10) pentapeptide shared by other family members. Overexpression of ICE LAP-6 induces apoptosis in MCF7 breast carcinoma cells. ICE LAP-6 is also proteolytically processed into an active cysteine protease by granzyme B, an important component of cytotoxic T cell-mediated apoptosis. Once activated, ICE LAP-6 is able to cleave the death substrate poly (ADP-ribose) polymerase (PARP) into signature apoptotic fragments.

Overexpression of ICE LAP-6 in MCF7 breast carcinoma cells induces cell death and mutation of the putative catalytic cysteine residue abolishes its apoptotic potential. Furthermore, granzyme B directly activates ICE LAP-6 and Yama in vitro, suggesting that granzyme B may mediate its cytotoxic effect via activation of several ICE/Ced-3 family members. Once activated, Yama and ICE LAP-6 are both able to cleave the DNA repair enzyme poly (ADP-ribose) polymerase (PARP) into signature apoptotic fragments. Taken together, these results indicate that ICE LAP-6, like other members of the Ced-3 subfamily, likely plays an important role in the apoptotic mechanism.

Cloning of ICE LAP-6

A cDNA corresponding to the partial open reading frame of ICE LAP-6 was identified as a sequence homologous to ICE LAP-3 (Duan, H., et al. (1996) J. Biol. Chem. 271, 35013–35035) on searching database comprising ESTs made by established EST methods (Adams, M. D., et al. (1991) Science 252, 1651–1656; Adams, M. D., et al (1992) Nature 355, 632–634). A novel cDNA clone, encoding a partial open reading frame, was identified and showed sequence homology with members of the ICE/ced-3 gene family. Of 22 positive clones, 6 clones yielded a 2.3 kb cDNA containing an 1252-base pair open reading frame that encoded a novel protein with a predicted molecular weight of 45.8 kD, designated ICE LAP-6 (see FIG. 1). The putative initiator methionine (GCCATGG; Met codon underlined) was in agreement with the consensus Kozak's sequence for translation initiation (Kozak. M. (1989) J Cell Biol 108, 229–241). This clone contains an open reading frame encoding the C-terminal 300 amino acids of ICE LAP-6. Full length cDNAs were obtained by screening an oligo-d(T) primed cDNA library of the human chronic myelogenous leukemia cell line K562. Approximately, $1 \times 10^6$ transformants were screened with a $^{32}$P-labeled DNA fragment generated by PCR, corresponding to nucleotides 615 to 940 of the ICE LAP-6 open reading frame (Sambrook, J., et al (1989) Molecular Cloning: A Laboratory Manual, Second Edition, Cold spring Harbor Laboratory Press, New York). Double-stranded DNA sequencing was carried out by the dideoxy chain termination method using modified T7 DNA polymerase (Sequenase, United States Biochemical Corporation). Sequence alignments were performed using DNASTAR Megalign software.

Northern Blot

Analyses of Adult and fetal human multiple tissue Northern blots (Clontech) containing 2 µg/lane poly(A)$^+$RNA were hybridized, according to the manufacturer's instructions, using the same $^{32}$P-labeled ICE LAP-6 probe used for library screening.

Expression Vectors

The DNA inserts encoding the C-terminal FLAG-tagged (ICE LAP-6 flag) or His6-tagged (ICE LAP-6 His) ICE LAP-6 were generated by PCR and subcloned into the mammalian expression vector pcDNA3 (Invitrogen). The 5' PCR primer (GAACGGGGTACCGCCATGGAC-GAAGCGGATCGGC) [SEQUENCE ID NO. 5] contained a KpnI restriction site and the two 3' primers (TGCTCTA-GATTACTTGTCATCGTCGTCCFTG-TAGTCTGATGTTTTAAAGT TAAGTTTTTTCCGGAG) [SEQUENCE ID NO. 9] or CTGCTCTAGATTAGTGGTG-GTGGTGGTGGTGTGATGTTTTAAAGAAAAGT TTTTTCCGGAG) [SEQUENCE ID NO. 6] encoded a FLAG epitope tag (DYKDDDDK) or a His6 tag, respectively. Alteration of the active site cysteine 286 to an alanine was accomplished by site-directed mutagenesis employing a four-primer PCR-based method (Higuchi, R, et al (1988) Nucleic Acids Research 16, 7351–7367). The mutagenetic oligonucleotides were AAGCTCTTTTTCATCCAGGC-CGCGGGTGGGGAGCAGAAGAC [SEQUENCE ID NO. 7] and GTCTTTCTGCTCCCCACCCGCGGCCTG-GATGAAAAAAGC [SEQUENCE ID NO. 8]. The presence of the introduced mutation and fidelity of PCR replication were confirmed by sequence analysis.

Apoptosis Assays

MCF7 breast carcinoma cells were transiently transfected as described previously (Chinnaiyan, A. M., et al (1995) Cell 81, 505–512). Briefly, $2.5 \times 10^5$ MCF7 cells were transfected with 0.25 µg of the reporter plasmid pCMV β-galactosidase plus 1 µg of test plasmid in 6-well tissue culture dishes using lipofectamine as per manufacturer's instructions. The transfection was carried out in 1 ml of Opti-MEM Minimal Media (GMBCO-BRL) and after 5 hours, 1 ml of serum-containing growth media was added. Two days later, the cells were fixed with 0.5% glutaraldehyde and stained with X-gal for 4 hours. Cells were visualized by phase-contrast microscopy. At least 300 β-galactosidase-positive cells were counted for each transfection (n=3) and identified as apoptotic or nonapoptotic based on morphological alterations typical of adherent cells undergoing apoptosis including becoming rounded, condensed, and detaching from the dish (Cohen, J. J. (1993) Immunology Today 14, 126–130). Expression and Purification of His6-Tagged Yama and His6-tagged ICE LAP-6 and $^{35}$S-labeled Yama and ICE LAP-6 proteins were generated by in vitro transcription/translation using the TNT kit (Promega) according to the instructions of the manufacturer, the template plasmids were ICE LAP-6 His and Yama His (Tewari, M., et al. (1995) Cell 81, 801–809). The translated proteins were purified by chromatography as described previously (Tewari, At, et al. (1995) Cell 81, 801–809). Activation of ICE LAP-6 and Yama by Granzyme B-Purified in vitro-translated pro-ICE LAP-6 or pro-Yama was activated by incubation with granzyme B as described previously (Quan, L. T., et al (1996) PNAS 93, In Press). Briefly, 48 ml of $^{35}$S-labeled protein was incubated with 20 pmole of purified granzyme B (22) in a total volume of 50 µl. After 4 hours, 20 ml of reaction was removed for SDS-PAGE analysis. 520 pmole of anti-GraB (Quan. L. T., et al (1996) PNAS 93, In Press) was added to the rest of the reaction mix to neutralize granzyme B activity. Following a 15 min incubation, 1 ml (150 mg) of purified PARP Tewari, M., et al. (1995) Cell 81, 801–809) was added and the reaction was allowed to proceed for 2 hours. The control reaction containing PARP alone or PARP plus granzyme B and antiGraB was carried out under identical conditions, except that Yama or ICE LAP-6 was not added. The reaction buffer contained 50 mM Hepes (pH 7.4), 0.1 M NaCl, 0.1% CHAPs, and 10% sucrose. All incubations were carried out at 37° C. in 10 mM DTT. Samples were analyzed by immunoblotting with anti-PARP monoclonal antibody C-2-10 as described previously Tewari, M., et al. (1995) Cell 81, 801–809).

ICE LAP-6 is a Novel Member of the ICE/ced-3 Gene Family

A blast search of GenBank protein data base revealed that the predicted protein sequence of ICE LAP-6 has significant similarity to the members of the ICE/Ced-3 family, particularly in the regions corresponding to the active subunits of ICE (Thomberry, N. A.,et al (1992) Nature 356, 768–774). In this region, ICE LAP-6 shares 31% sequence identity (55% sequence similarity) with the C. elegans CED-3 protein, 33% identity (52% sequence similarity) with ICE-LAP3, 30% identity (56% similarity) with Mch2a and 29% sequence identity (52% similarity) with Yama. ICE LAP-6 also has 25%–28% sequence identity with ICE and the ICE-related genes, ICE rel II and ICE rel III. Phylogenetic analysis of the ICE/ced-3 gene family showed that ICE LAP-6 is a member of the Ced-3 subfamily which includes Yama, ICE-LAP3, and Mcb2 (FIG. 5). Like Ced-3, ICE LAP-6 contains a long N-terminal putative prodorpain. Based on the x-ray crystal structure of ICE (Walker, N. P. C. et al, (1994) Cell 78, 343–352; Wilson, K. P., et al (1994) Nature 370, 270–275), the amino acid residues His237, Gly238, Cys285 of ICE are involved in catalysis, while the residues Arg 179, Gln283 and Arg341form a binding pocket for the carboxylate side chain of the P1 aspartic acid. These six residues are conserved in all ICE/Ced-3 family members thus far cloned as well as in ICE LAP-6. However, residues that form the P2–P4 binding pockets are not widely conserved among family members, suggesting that they may determine substrate specificity. Surprisingly, ICE LAP-6 contains a unique active site pentapeptide QACGG, instead of the QACRG shared by other family members (FIG. 2).

Distribution of ICE LAP-6

Northern blot analysis revealed that ICE LAP-6 is constitutively expressed in a variety of human tissues. Two ICE LAP-6 mRNA transcripts were detected. The 2.3 kilobase transcript corresponds to the size of the cDNA clones isolated from the K562 library. The other transcript, which is approximately 3 kb, is believed to represent an alternatively spliced ICE LAP-6 isoform.

Overexpression of ICE LAP-6 in MCF7 Cells Induces Apoptosis

Figure 6:
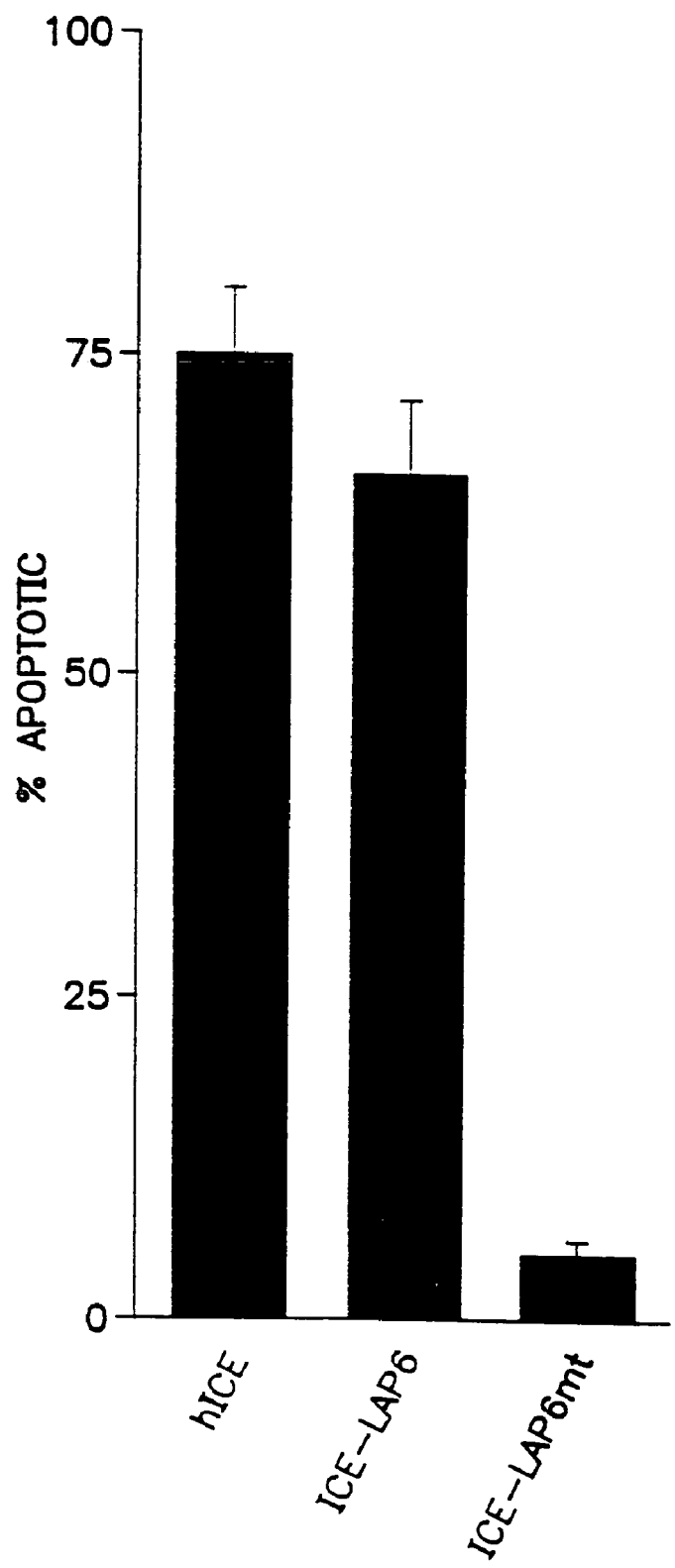
FIG. 6 shows MCF7 the results of an analysis of breast carcinoma cells transiently transfected demonstrating that over-expression of ICE LAP-6 induces cell death in mammalian cells.

To study the functional role of ICE LAP-6, MCF7 breast carcinoma cells were transiently transfected with an expression vector encoding the full-length ICE LAP-6 protein (ICE LAP-6-flag) and subsequently assessed for apoptotic features. Like the other ICE/Ced-3 family members, expression of ICE LAP-6 caused cell death (FIG. 6) The ICE LAP-6-transfected MCF7 cells displayed morphological alterations typical of adherent cells undergoing apoptosis, becoming rounded, condensed, and detaching from the dish. ICE LAP-6 induced apoptosis was inhibited by the broad spectnn ICE inhibitor z-VAD fmk (Pronk, G. J., (1996) Science 271, 808–810). To determine whether the amino acid residue Cys286, corresponding to the catalytic Cys285 of ICE, was essential for apoptotic activity, a mutant form of ICE LAP-6 was generated in which the cysteine residue was altered to an alanine. MCF7 breast carcinoma cells were transiently transfected with the reporter gene b-galactosidase and either C-terminal flag-tagged ICE LAP-6, the mutant version with the catalytic cysteine residue inactivated (ICE LAP-6 mt) or ICE as described elsewhere herein. Percent apoptotic cells represents the mean value from three independent experiments. As predicted, overexpression of the mutant form of ICE LAP-6 did not induce apoptotic changes in MCF7 cells (FIG. 6). Furthermore, these results demonstrate that an ICE/Ced-3 family member containing an active site QACGG (SEQ ID NO:11) pentapeptide (rather than QACRG (SEQ ID NO:10)) may still possess apoptosis-inducing potential and presumably enzymatic activity.

Proteolytic Activation of ICE LAP-6 by Granzyme B

Members of the ICE/ced-3 gene family are synthesized as proenzymes and activated by proteolytic cleavage at specific aspartate residues to form heterodimeric enzymes. In ICE, this cleavage removes the prodomain and produces a heterodimeric complex consisting of p20 and p10 subunits (Thomberry, N. A., et al (1992) Nature 356, 768–774). Similarly, activated Yama is comprised of two subunits, p17 and p12, which are derived from a 32 kDa proenzyme Nicholson, D. Wet al. (1995) Nature 376, 37–43). The mechanism by which death signals activate ICE/Ced-3 family members is poorly understood Recent studies on granzyme B, however, suggest that cytotoxic T cells may utilize this secreted serine protease to directly activate members of the ICB/Ced-3 family. It has been demonstrated that granzyme B can proteolytically activate pro-Yama, generating an active enzyme capable of cleaving the death substrate PARP into characteristic fragments (Darmon, A. J., et al (1995) Nature 377, 446–448). By contrast, ICE, although cleaved by granzyme B, fails to be activated. Thus, it was determined whether ICE LAP-6 can serve as a substrate for granzyme B. His6 tagged ICE LAP-6 and Yama were generated by in vitro transcription/translation, and subsequently purified by Ni-affinity chromatography as described elsewhere herein. The purified in vitro-translated pro-ICE LAP-6 or pro-Yama was incubated with purified granzyme B (Hanna, W. L., et al (1993) Protein Expr Purif 4, 398–404; Quan, L. T., et al (1995) Journal of Biological Chemistry 270, 10377–10379). After 4 hours at 37° C., ICE LAP-6 was proteolytically processed into 3 fragments. The two low molecular weight bands represent the active subunits of ICE LAP-6 and correspond to the p17 and p12 subunits of active Yama. The 32 kDa band is an likely intermediate, in which only the pro-domain is removed (a similar intermediate is generated in the activation of ICE LAP-3) Duan, H., et al. (1996) J. Biol. Chem. 271, 35013–35035; Chinnaiyan, A. M., et al. 1996) Journal of Biological Chemistry 271, 4573–4576). Next, granzyme B-mediated cleavage of ICE LAP-6 was assessed for generation of an active enzyme by assaying for PARP cleavage. PARP is proteolyzed during many forms of apoptosis, and the enzyme(s) responsible is likely of the ICE/Ced-3 family. To exclude the possibility of direct cleavage of PARP by granzyme B, granzyme B-processed ICE LAP-6 and Yama were incubated with a selective inhibitor of granzyme B (anti-GraB). Both granzyme B-processed Yama and ICE LAP-6 were active as determined by their ability to cleave PARP. Unlike ICE, ICE LAP-6 and other members of the Ced-3 subfamily are able to cleave the PARP into signature apoptotic fragments (Tewari, M., et al. (1995) Cell 81, 801–809; Femandes-Alnemri, T., et al. (1994) J. Biol. Chen 269, 30761–30764—Nicholson, D. Wet al. (1995) Nature 376, 37–43; Femandes-Alnemri, T., et al. (1995) Cancer Research 55, 6045–6052; Lippke, J. A., et al. (1996) The Journal of Biological Chemistry 271, 1825–1828; Femandes-Alnemri, T., et al. (1995) Cancer Res 55, 2737–2742).

Provided by the present invention is a novel member of the ICE/Ced-3 family of cysteine proteases. ICE LAP-6 has a unique active site QACGG (SEQ ID NO:11) pentapeptide and is classified in the subfamily most related to Ced-3 and Yama. Ectopic expression of ICE LAP-6 in mammalian cells causes apoptosis.

Importantly, ICE LAP-6, like Yama, was directly activated by granzyme B in vitro, suggesting that cytotoxic T cells may mediate apoptosis by activating more than one ICE/Ced-3 family member in susceptible target cells. Yama, ICE-LAP3, and now ICE LAP-6, have been shown to be proteolytically activated by apoptotic stimuli.

Example 2

Gene Therapeutic Expression of Human ICE LAP-6

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flash The flask is turned upside down, closed tight and left at room temperature overnight After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

ICE LAP-6 cDNA capable of expressing active ICE LAP-6, is isolated. The ends of the fragment are modified, if necessary, for cloning into the vector. For instance, 5' overhanging may be treated with DNA polymerase to create blunt ends. 3' overhanging ends may be removed using S1 nuclease. Linkers may be ligated to blunt ends with T4 DNA ligase.

Equal quantities of the Moloney murine leukemia virus linear backbone and the ICE LAP-6 fragment are mixed together and joined using T4 DNA ligase. The ligation mixture is used to transform E. coli and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the ICE LAP-6 gene is introduced into the packaging cells by standard techniques. Infectious viral particles containing the ICE LAP-6 gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce ICE LAPS product, and the biological actions of the protein are conveyed to the host.

It will be clear that the invention may be practiced otherwise than as particularly described in the foregoing description and examples.

Numerous modifications and variations of the present invention are possible in light of the above teachings and, therefore, are within the scope of the appended claims.

What is claimed is:

1. An isolated protein which comprises amino acid residues 2 to 416 of SEQ ID NO:1.

2. The isolated protein of claim 1 wherein the amino acid residues are fused to a heterologous polypeptide.

3. A composition comprising the protein of claim 1 and a pharmaceutically acceptable carrier.

4. An isolated protein produced by a method comprising:
   (a) culturing a host cell under conditions suitable to produce the protein of claim 1; and
   (b) recovering the protein of claim 1 from the host cell culture.

5. An isolated protein comprising a polypeptide sequence which is at least 95% identical to amino acid residues 2 to 416 of SEQ ID NO:1, wherein said protein induces apoptosis.

6. The isolated protein of claim 5 wherein the polypeptide sequence is fused to a heterologous polypeptide.

7. A composition comprising the protein of claim 5 and a pharmaceutically acceptable carrier.

8. An isolated protein produced by a method comprising:
   (a) culturing a host cell under conditions suitable to produce the protein of claim 5; and
   (b) recovering the protein of claim 5 from the host cell culture.

9. An isolated protein consisting of at least 30 contiguous amino acid residues of amino acids 1 to 416 of SEQ ID NO:1 wherein said isolated protein binds to an antibody that binds to amino acid residues 1 to 416 of SEQ ID NO: 1.

10. The isolated protein of claim 9 which consists of at least 50 contiguous amino acid residues of amino acids 1 to 416 of SEQ ID NO:1 wherein said isolated protein binds to an antibody that binds to amino acid residues 1 to 416 of SEQ ID NO: 1.

11. The isolated protein of claim 9 wherein the amino acid residues are fused to a heterologous polypeptide.

12. A composition comprising the protein of claim 9 and a pharmaceutically acceptable carrier.

13. An isolated protein produced by a method comprising:
   (a) culturing a host cell under conditions suitable to produce the protein of claim 9; and
   (b) recovering the protein of claim 9 from the host cell culture.

14. An isolated protein which comprises the amino acid sequence of the full-length polypeptide encoded by the cDNA contained in ATCC™ Deposit No. 95590, excepting the N-terminal methionine.

15. The isolated protein of claim 14 wherein the amino acid sequence is fused to a heterologous polypeptide.

16. A composition comprising the protein of claim 14 and a pharmaceutically acceptable carrier.

17. An isolated protein produced by a method comprising:
   (a) culturing a host cell under conditions suitable to produce the protein of claim 14; and
   (b) recovering the protein of claim 14 from the host cell culture.

18. An isolated protein comprising a polypeptide sequence which is at least 95% identical to the amino acid sequence of the full-length polypeptide encoded by the cDNA contained in ATCC™ Deposit No. 95590, excepting the N-terminal methionine, wherein said protein induces apoptosis.

19. The isolated protein of claim 18 wherein the polypeptide sequence is fused to a heterologous polypeptide.

20. A composition comprising the protein of claim 18 and a pharmaceutically acceptable carrier.

21. An isolated protein produced by a method comprising:
   (a) culturing a host cell under conditions suitable to produce the protein of claim 18; and
   (b) recovering the protein of claim 18 from the host cell culture.

22. An isolated protein consisting of at least 30 contiguous amino acid residues of the full-length polypeptide encoded by the cDNA contained in ATCC™ Deposit No. 95590 wherein said isolated protein binds to an antibody that binds to the full-length polypeptide encoded by the cDNA contained in ATCC™ Deposit No. 97590.

23. The isolated protein of claim 22 which consists of at least 50 contiguous amino acid residues of the full-length polypeptide encoded by the cDNA contained in ATCC™ Deposit No. 95590 wherein said isolated protein binds to an antibody that binds to the full-length polypeptide encoded by the cDNA contained in ATCC™ Deposit No. 97590.

24. The isolated protein of claim 22 wherein the amino acid residues are fused to a heterologous polypeptide.

25. A composition comprising the protein of claim 22 and a pharmaceutically acceptable carrier.

26. An isolated protein produced by a method comprising:
   (a) culturing a host cell under conditions suitable to produce the protein of claim 22; and
   (b) recovering the protein of claim 22 from the host cell culture.

* * * * *

UNITED STATES PATENT AND TRADEMARK OFFICE
CERTIFICATE OF CORRECTION

PATENT NO. : 7,115,260 B2
APPLICATION NO. : 10/961148
DATED : October 3, 2006
INVENTOR(S) : Dixit et al.

It is certified that error appears in the above-identified patent and that said Letters Patent is hereby corrected as shown below:

In The Specification:

Column 1, line 64, delete "alight" and insert --might--;

Column 1, line 67, delete "Gagliarnini," and insert --Gagliardini,--;

Column 1, line 67, delete "826:828" and insert --826-828--;

Column 2, line 18, delete "1525612" and insert --15256--;

Column 2, line 25, delete "Fernandes-Alnemri," and insert --(Fernandes-Alnemri--;

Column 2, line 37, delete "uan," and insert --Duan,--;

Column 2, line 54, delete "1996)" and insert --(1996)--;

Column 3, line 25, delete "cererbellar" and insert --cerebellar--;

Column 11, line 67, delete "polyp eptide" and insert --polypeptide--;

Column 16, line 36, delete "of," and insert --of--;

Column 17, line 17, delete "several" and insert --several,--;

Column 17, line 23, delete "as amino" and insert --as 5 amino--;

Column 17, line 45, delete "about" and insert --above--;

Column 18, line 27, delete "correspondent" and insert --correspond--;

Column 24, line 29, delete "ICE LAPS" and insert --ICE LAP-6--;

Column 27, line 18, delete "aid" and insert --air--;

Column 27, line 34, delete "medium Slides" and insert --medium. Slides--;

Column 29, line 20, delete "out Reagents" and insert --out. Reagents--;

UNITED STATES PATENT AND TRADEMARK OFFICE
CERTIFICATE OF CORRECTION

PATENT NO. : 7,115,260 B2
APPLICATION NO. : 10/961148
DATED : October 3, 2006
INVENTOR(S) : Dixit et al.

It is certified that error appears in the above-identified patent and that said Letters Patent is hereby corrected as shown below:

In The Specification (cont'd):

Column 31, line 58, delete "Antoher" and insert --Another--;

Column 33, line 42, delete "art For" and insert --art. For--;

Column 37, line 46, delete "prodorpain" and insert --prodomain--;

In The Claims:

Col. 49, Claim 14, line 46, delete "95590" and insert --97590--;

Col. 50, Claim 18, line 13, delete "95590" and insert --97590--;

Col. 50, Claim 22, line 27, delete "95590" and insert --97590--; and

Col. 50, Claim 23, line 34, delete "95590" and insert --97590--.

Signed and Sealed this

Fourth Day of September, 2007

JON W. DUDAS
*Director of the United States Patent and Trademark Office*

SEQUENCE LISTING

<160> NUMBER OF SEQ ID NOS: 11

<210> SEQ ID NO 1
<211> LENGTH: 416
<212> TYPE: PRT
<213> ORGANISM: Homo sapiens

<400> SEQUENCE: 1

```
Met Asp Glu Ala Asp Arg Arg Leu Leu Arg Arg Cys Arg Leu Arg Leu
 1               5                  10                  15

Val Glu Glu Leu Gln Val Asp Gln Leu Trp Asp Val Leu Leu Ser Arg
             20                  25                  30

Glu Leu Phe Arg Pro His Met Ile Glu Asp Ile Gln Arg Ala Gly Ser
         35                  40                  45

Gly Ser Arg Arg Asp Gln Ala Arg Gln Leu Ile Ile Asp Leu Glu Thr
     50                  55                  60

Arg Gly Ser Gln Ala Leu Pro Leu Phe Ile Ser Cys Leu Glu Asp Thr
 65                  70                  75                  80

Gly Gln Asp Met Leu Ala Ser Phe Leu Arg Thr Asn Arg Gln Ala Gly
                 85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
            115                 120                 125

Val Asp Ile Gly Ser Gly Gly Phe Gly Asp Val Gly Ala Leu Glu Ser
    130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Leu His Phe Met Val Glu Val Lys Gly Asp Leu Thr
            195                 200                 205

Ala Lys Lys Met Val Leu Ala Leu Leu Glu Leu Ala Arg Gln Asp His
    210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
            275                 280                 285

Gly Glu Gln Lys Asp His Gly Phe Glu Val Ala Ser Thr Ser Pro Glu
    290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
            355                 360                 365

Asp Ile Phe Glu Gln Trp Ala His Ser Glu Asp Leu Gln Ser Leu Leu
    370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415
```

-continued

<210> SEQ ID NO 2
<211> LENGTH: 1578
<212> TYPE: DNA
<213> ORGANISM: Homo sapiens
<220> FEATURE:
<221> NAME/KEY: misc_feature
<222> LOCATION: (1357)..(1357)
<223> OTHER INFORMATION: n = a, c, g, or t
<220> FEATURE:
<221> NAME/KEY: misc_feature
<222> LOCATION: (1481)..(1481)
<223> OTHER INFORMATION: n = a, c, g, or t

<400> SEQUENCE: 2

| | | | | | |
|---|---|---|---|---|---|
| gccatggacg | aagcggatcg | gcggctcctg | cggcggtgcc | ggctgcggct | ggtggaagag | 60 |
| ctgcaggtgg | accagctctg | ggacgtcctg | ctgagccgcg | agctgttcag | gccccatatg | 120 |
| atcgaggaca | tccagcgggc | aggctctgga | tctcggcggg | atcaggccag | gcagctgatc | 180 |
| atagatctgg | agactcgagg | gagtcaggct | cttcctttgt | tcatctcctg | cttagaggac | 240 |
| acaggccagg | acatgctggc | ttcgtttctg | cgaactaaca | ggcaagcagg | aaagttgtcg | 300 |
| aagccaaccc | tagaaaacct | taccccagtg | gtgctcagac | cagagattcg | caaaccagag | 360 |
| gttctcagac | cggaaacacc | cagaccagtg | gacattggtt | ctggaggatt | cggtgatgtc | 420 |
| ggtgctcttg | agagtttgag | gggaaatgca | gatttggctt | acatcctgag | catggagccc | 480 |
| tgtggccact | gcctcattat | caacaatgtg | aacttctgcc | gtgagtccgg | gctccgcacc | 540 |
| cgcactggct | ccaacatcga | ctgtgagaag | ttgcggcgtc | gcttctcctc | gctgcatttc | 600 |
| atggtggagg | tgaagggcga | cctgactgcc | aagaaaatgg | tgctggcttt | gctggagctg | 660 |
| gcgcggcagg | accacggtgc | tctggactgc | tgcgtggtgg | tcattctctc | tcacggctgt | 720 |
| caggccagcc | acctgcagtt | cccaggggct | gtctacggca | cagatggatg | ccctgtgtcg | 780 |
| gtcgagaaga | ttgtgaacat | cttcaatggg | accagctgcc | ccagcctggg | agggaagccc | 840 |
| aagctctttt | tcatccaggc | ctgtggtggg | gagcagaaag | accatgggtt | tgaggtggcc | 900 |
| tccacttccc | ctgaagacga | gtcccctggc | agtaaccccg | agccagatgc | caccccgttc | 960 |
| caggaaggtt | tgaggacctt | cgaccagctg | gacgccatat | ctagtttgcc | cacacccagt | 1020 |
| gacatctttg | tgtcctactc | tactttccca | ggttttgttt | cctggaggga | ccccaagagt | 1080 |
| ggctcctggt | acgttgagac | cctggacgac | atctttgagc | agtgggctca | ctctgaagac | 1140 |
| ctgcagtccc | tcctgcttag | ggtcgctaat | gctgtttcgg | tgaaagggat | ttataaacag | 1200 |
| atgcctggtt | gctttaattt | cctccggaaa | aaacttttct | ttaaaacatc | ataaggccag | 1260 |
| ggcccctcac | cctgccttat | cttgcacccc | aaagctttcc | tgccccaggc | ctgaaagagg | 1320 |
| ctgaggcctg | gactttcctg | caactcaagg | actttgnagc | cggcacaggg | tctgctcttt | 1380 |
| ctctgccagt | gacagacagg | ctcttagcag | cttccagatt | gacgacaagt | gctgaacagt | 1440 |
| ggaggaagag | ggacagatga | atgccgtgga | ttgcacgtgg | nctcttgagc | agtggctggt | 1500 |
| ccagggctag | tgacttggtg | tcccatgatc | cctgtgttgg | tctctaggag | cagggattaa | 1560 |
| cctctgcact | actgacat | | | | | 1578 |

<210> SEQ ID NO 3
<211> LENGTH: 639
<212> TYPE: DNA
<213> ORGANISM: Homo sapiens

<400> SEQUENCE: 3

| | | | | | |
|---|---|---|---|---|---|
| ctgactgcca | agaaaatggt | gctggctttg | ctggagctgg | cgcggcagga | ccacggtgct | 60 |

-continued

```
ctggactgct gcgtggtggt cattctctct cacggctgtc aggccagcca cctgcagttc      120 ccagggctg tctacggcac agatggatgc cctgtgtcgg tcgaaaagat tgtgaacatc       180
ttcaatggga ccagctgccc cagcctggga gggaagccca agctcttttt catccaggcc     240
tgtggtgggg agcagaaaga ccatgggttt gaggtggcct ccacttcccc tgaagacgag     300
tcccctggca gtaaccccga gccagatgcc accccgttcc aggaaggttt gaggaccttc     360
gaccagctgg acgccatatc tagtttgccc acacccagtg acatctttgt gtcctactct     420
actttcccag gttttgtttc ctggagggac cccaagagtg gctcctggta cgttgagacc     480
ctggacgaca tctttgagca gtgggctcac tctgaagacc tgcagtccct cctgcttagg     540
gtcgctaatg ctgtttcggt gaaagggatt tataaacaga tgcctggttg ctttaatttc     600
ctccggaaaa aacttttctt ttaaaacatc ataaggcag                             639
```

<210> SEQ ID NO 4
<211> LENGTH: 203
<212> TYPE: PRT
<213> ORGANISM: Homo sapiens

<400> SEQUENCE: 4

```
Met Val Leu Ala Leu Glu Leu Ala Arg Gln Asp His Gly Ala Leu
1               5                  10                  15

Asp Cys Cys Val Val Ile Leu Ser His Gly Cys Gln Ala Ser His
                20                  25                  30

Leu Gln Phe Pro Gly Ala Val Tyr Gly Thr Asp Gly Cys Pro Val Ser
            35                  40                  45

Val Glu Lys Ile Val Asn Ile Phe Asn Gly Thr Ser Cys Pro Ser Leu
        50                  55                  60

Gly Gly Lys Pro Lys Leu Phe Phe Ile Gln Ala Cys Gly Gly Glu Gln
65                  70                  75                  80

Lys Asp His Gly Phe Glu Val Ala Ser Thr Ser Pro Glu Asp Glu Ser
                85                  90                  95

Pro Gly Ser Asn Pro Glu Pro Asp Ala Thr Pro Phe Gln Glu Gly Leu
            100                 105                 110

Arg Thr Phe Asp Gln Leu Asp Ala Ile Ser Ser Leu Pro Thr Pro Ser
        115                 120                 125

Asp Ile Phe Val Ser Tyr Ser Thr Phe Pro Gly Phe Val Ser Trp Arg
130                 135                 140

Asp Pro Lys Ser Gly Ser Trp Tyr Val Glu Thr Leu Asp Asp Ile Phe
145                 150                 155                 160

Glu Gln Trp Ala His Ser Glu Asp Leu Gln Ser Leu Leu Leu Arg Val
                165                 170                 175

Ala Asn Ala Val Ser Val Lys Gly Ile Tyr Lys Gln Met Pro Gly Cys
            180                 185                 190

Phe Asn Phe Leu Arg Lys Lys Leu Phe Phe Met
        195                 200
```

<210> SEQ ID NO 5
<211> LENGTH: 34
<212> TYPE: DNA
<213> ORGANISM: Artificial
<220> FEATURE:
<223> OTHER INFORMATION: 5' PCR primer

<400> SEQUENCE: 5

```
gaacggggta ccgccatgga cgaagcggat cggc                                   34
```

```
<210> SEQ ID NO 6
<211> LENGTH: 60
<212> TYPE: DNA
<213> ORGANISM: Artificial
<220> FEATURE:
<223> OTHER INFORMATION: 3' PCR primer

<400> SEQUENCE: 6
tgctctagat tagtggtggt ggtggtggtg tgatgtttta agaaaagtt ttttccggag      60

<210> SEQ ID NO 7
<211> LENGTH: 41
<212> TYPE: DNA
<213> ORGANISM: Artificial
<220> FEATURE:
<223> OTHER INFORMATION: PCR primer

<400> SEQUENCE: 7
aagctctttt tcatccaggc cgcgggtggg gagcagaaga c                         41

<210> SEQ ID NO 8
<211> LENGTH: 39
<212> TYPE: DNA
<213> ORGANISM: Artificial
<220> FEATURE:
<223> OTHER INFORMATION: PCR primer

<400> SEQUENCE: 8
gtctttctgc tccccacccg cggcctggat gaaaaaagc                            39

<210> SEQ ID NO 9
<211> LENGTH: 66
<212> TYPE: DNA
<213> ORGANISM: Artificial
<220> FEATURE:
<223> OTHER INFORMATION: 3' PCR primer

<400> SEQUENCE: 9
tgctctagat tacttgtcat cgtcgtcctt gtagtctgat gttttaaagt taagtttttt     60
ccggag                                                                66

<210> SEQ ID NO 10
<211> LENGTH: 5
<212> TYPE: PRT
<213> ORGANISM: Homo sapiens

<400> SEQUENCE: 10

Gln Ala Cys Arg Gly
1               5

<210> SEQ ID NO 11
<211> LENGTH: 5
<212> TYPE: PRT
<213> ORGANISM: Homo sapiens

<400> SEQUENCE: 11

Gln Ala Cys Gly Gly
1               5
```